US010999569B2

(12) United States Patent
Eckhouse et al.

(10) Patent No.: US 10,999,569 B2
(45) Date of Patent: May 4, 2021

(54) THREE-DIMENSIONAL IMAGE RECONSTRUCTION USING MULTI-LAYER DATA ACQUISITION

(71) Applicant: EVA—ESTHETIC VISUAL ANALYTICS LTD., Yokneam (IL)

(72) Inventors: Vardit Eckhouse, Kerem Maharal (IL); David Aziz, Zichron Yaakov (IL)

(73) Assignee: EVA—ESTHETIC VISUAL ANALYTICS LTD., Yokneam (IL)

(*) Notice: Subject to any disclaimer, the term of this patent is extended or adjusted under 35 U.S.C. 154(b) by 0 days.

(21) Appl. No.: 16/472,981

(22) PCT Filed: Dec. 21, 2017

(86) PCT No.: PCT/IL2017/051374
§ 371 (c)(1),
(2) Date: Jun. 24, 2019

(87) PCT Pub. No.: WO2018/116304
PCT Pub. Date: Jun. 28, 2018

(65) Prior Publication Data
US 2020/0092534 A1    Mar. 19, 2020

Related U.S. Application Data

(60) Provisional application No. 62/437,881, filed on Dec. 22, 2016.

(51) Int. Cl.
*H04N 13/254* (2018.01)
*G06T 7/514* (2017.01)
(Continued)

(52) U.S. Cl.
CPC ......... *H04N 13/254* (2018.05); *A61B 5/0075* (2013.01); *A61B 5/0077* (2013.01);
(Continued)

(58) Field of Classification Search
CPC .. H04N 13/254; H04N 13/257; H04N 13/167; H04N 13/156; H04N 13/296;
(Continued)

(56) References Cited

U.S. PATENT DOCUMENTS 5,168,327 A    12/1992 Yamawaki
6,578,767 B1*   6/2003 Barkan ............. G06K 7/10772
                                                235/462.2
(Continued)

FOREIGN PATENT DOCUMENTS

CN    102494609 B    9/2013
WO    2012115862 A2   8/2012

OTHER PUBLICATIONS

Kim, Jun-Sik, and Takeo Kanade. "Multiaperture telecentric lens for 3D reconstruction." Optics letters 36.7 (2011):1050-1052.
(Continued)

*Primary Examiner* — Alexander Gee
(74) *Attorney, Agent, or Firm* — The Roy Gross Law Firm, LLC; Roy Gross

(57) ABSTRACT

A camera, including: two imaging systems each comprising a different optical path corresponding to a different viewing angle of an object; one or more illumination sources; a mask disposed with multiple pairs of apertures, wherein each aperture of each aperture pair corresponds to a different one of the imaging systems; at least one detector configured to acquire multiple image pairs of the object from the two imaging systems via the multiple pairs of apertures; and a processor configured to produce from the multiple acquired image pairs a multi-layer three dimensional reconstruction of the object.

20 Claims, 22 Drawing Sheets

(51) Int. Cl.
| | |
|---|---|
| *G06T 7/593* | (2017.01) |
| *H04N 13/257* | (2018.01) |
| *H04N 13/167* | (2018.01) |
| *H04N 13/156* | (2018.01) |
| *H04N 13/296* | (2018.01) |
| *H04N 13/239* | (2018.01) |
| *A61B 5/00* | (2006.01) |
| *G06T 7/00* | (2017.01) |
| *H04N 13/00* | (2018.01) |
| *G03B 35/12* | (2021.01) |
| *H04N 5/232* | (2006.01) |

(52) U.S. Cl.
CPC ............ *A61B 5/443* (2013.01); *G06T 7/0012* (2013.01); *G06T 7/514* (2017.01); *G06T 7/593* (2017.01); *H04N 5/232933* (2018.08); *H04N 13/156* (2018.05); *H04N 13/167* (2018.05); *H04N 13/239* (2018.05); *H04N 13/257* (2018.05); *H04N 13/296* (2018.05); *G06T 2207/10012* (2013.01); *H04N 2013/0077* (2013.01); *H04N 2013/0081* (2013.01)

(58) Field of Classification Search
CPC .... H04N 13/239; H04N 13/10; H04N 13/122; H04N 13/293; H04N 5/232933; H04N 2013/0077; H04N 2013/0081; H04N 2013/0074; G06T 7/514; G06T 7/593; G06T 7/0012; G06T 2207/10012; A61B 5/0075; A61B 5/0077; A61B 5/443
See application file for complete search history.

(56) References Cited

U.S. PATENT DOCUMENTS

| | | | | |
|---|---|---|---|---|
| 8,619,148 | B1* | 12/2013 | Watts | H04N 5/2258 348/218.1 |
| 2002/0149691 | A1 | 10/2002 | Pereira et al. | |
| 2003/0198377 | A1 | 10/2003 | Ng | |
| 2005/0043837 | A1 | 2/2005 | Rubbert et al. | |
| 2007/0171220 | A1 | 7/2007 | Kriveshko | |
| 2008/0013943 | A1* | 1/2008 | Rohaly | G03B 35/00 396/333 |
| 2008/0259354 | A1 | 10/2008 | Gharib et al. | |
| 2009/0022393 | A1 | 1/2009 | Bar-Zohar et al. | |
| 2009/0141966 | A1 | 6/2009 | Chen et al. | |
| 2009/0295908 | A1 | 12/2009 | Gharib et al. | |
| 2010/0209294 | A1* | 8/2010 | Owen | C02F 1/32 422/24 |
| 2011/0074932 | A1 | 3/2011 | Gharib et al. | |
| 2011/0206254 | A1* | 8/2011 | Patwardhan | A61B 5/0077 382/128 |
| 2013/0335417 | A1 | 12/2013 | McQuestion et al. | |
| 2014/0118500 | A1* | 5/2014 | Liu | H04N 13/204 348/46 |
| 2014/0120493 | A1 | 5/2014 | Levin | |
| 2014/0240354 | A1* | 8/2014 | Ma | G06T 19/006 345/633 |
| 2014/0340488 | A1* | 11/2014 | Shibazaki | H04N 5/23212 348/49 |
| 2014/0362186 | A1* | 12/2014 | Ji | H04N 13/246 348/46 |
| 2015/0011848 | A1 | 1/2015 | Ruchti | |
| 2015/0256813 | A1 | 9/2015 | Dal Mutto et al. | |
| 2015/0358613 | A1* | 12/2015 | Sandrew | H04N 13/261 348/36 |
| 2016/0154244 | A1* | 6/2016 | Border | G02B 27/0176 359/630 |
| 2016/0337612 | A1* | 11/2016 | Im | G06T 19/006 |
| 2016/0360104 | A1* | 12/2016 | Zhang | H04N 5/265 |
| 2017/0109888 | A1* | 4/2017 | de Lima | H04N 13/257 |
| 2019/0133513 | A1 | 5/2019 | Patwardhan | |

OTHER PUBLICATIONS

International Search Report of PCT/IL2017/051374 Completed Mar. 29, 2018; dated Mar. 29, 2018 3 pages.
Written Opinion of PCT/IL2017/051374 completed Mar. 29, 2018; dated Mar. 29, 2018 4 pages.
Kari Pulli and Linda G. Shapiro, "Surface Reconstruction and Display from Range and Color Data", Graphical Models 62, 165-201 (2000).

* cited by examiner

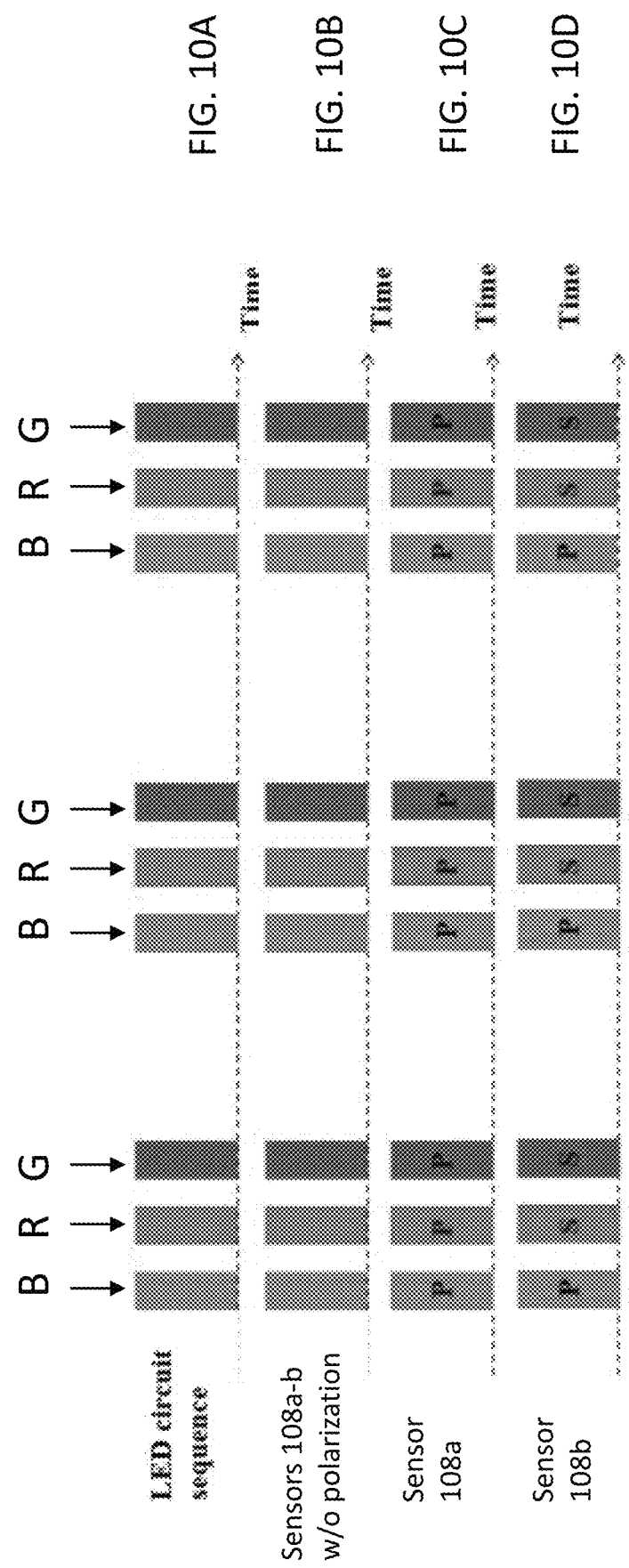

THREE-DIMENSIONAL IMAGE RECONSTRUCTION USING MULTI-LAYER DATA ACQUISITION

CROSS-REFERENCE TO RELATED APPLICATIONS

This application is a National Phase of PCT Patent Application No. PCT/IL2017/051374 having International filing date of Dec. 21, 2017, which claims the benefit of priority of U.S. Provisional Patent Application No. 62/437,881 filed Dec. 22, 2016. The contents of the above applications are all incorporated by reference as if fully set forth herein in their entirety.

BACKGROUND

The invention relates to the field of three-dimensional (3D) imaging.

Conventional cameras transform a three-dimensional view of an object into a two dimensional image. Typically, the depth dimension, corresponding to the distance between the focal plane of the captured image and the camera, is lost. To include a depth characteristic, some optical systems use two cameras to capture a pair of stereo images of the object, much the way our eyes work. Each image of the pair is acquired from a slightly different viewing angle, and the discrepancy between the two images is used to measure depth.

The foregoing examples of the related art and limitations related therewith are intended to be illustrative and not exclusive. Other limitations of the related art will become apparent to those of skill in the art upon a reading of the specification and a study of the figures.

SUMMARY

The following embodiments and aspects thereof are described and illustrated in conjunction with systems, tools and methods which are meant to be exemplary and illustrative, not limiting in scope.

One embodiment provides a camera, comprising: two imaging systems each comprising a different optical path corresponding to a different viewing angle of an object; one or more illumination sources; a mask comprising multiple pairs of apertures, wherein each aperture of each aperture pair corresponds to a different one of the imaging systems; at least one detector configured to acquire multiple image pairs of the object from the two imaging systems via the multiple pairs of apertures; and a processor configured to produce, from the multiple acquired image pairs, a multi-layer three dimensional reconstruction of the object.

In some embodiments, said one or more illumination sources are multiple illumination sources, and wherein each pair of apertures is dedicated to a different one of the multiple illumination sources.

In some embodiments, said multiple illumination sources comprise a red LED, a green LED, and a blue LED.

In some embodiments, each of the multiple different LEDs has a full-width-at-half (FWHM) bandwidth of 10 nm±10%.

In some embodiments, the at least one detector comprises a mono sensor having a dedicated region for each aperture, and configured to simultaneously capture multiple images comprising an image for each of the multiple illumination sources and for each of the imaging systems.

In some embodiments, the at least one detector comprises two imaging sensors that are each dedicated to one of the imaging systems and are configured to simultaneously detect an image pair for each of the illumination sources.

In some embodiments, the at least one detector comprises an imaging sensor having multiple sensor regions, each sensor region dedicated to a different one of the multiple apertures, and wherein the multiple sensor regions are configured to simultaneously capture multiple images comprising an image for each of the multiple illumination sources and for each of the imaging systems.

In some embodiments, at least one of the multiple different illumination sources is disposed with a polarization component, and wherein at least one of the apertures dedicated to the illumination source disposed with the polarization component, is disposed with a complementary polarization component.

In some embodiments, the at least one of the apertures disposed with the polarization component is dedicated to a blue light source.

In some embodiments, each pair of apertures is disposed with a color filter corresponding to its dedicated illumination source.

In some embodiments, the camera further comprises at least one back lens configured to focus light transmitted via the multiple pairs of apertures of the mask to the at least one detector.

In some embodiments, at least one image pair of the acquired image pairs corresponds to a specular reflection off the object, and wherein the processor is further configured to use the at least one image pair to measure a depth characteristic of the object.

In some embodiments, the processor is further configured to apply a shift to the pixels of the acquired image as a function of the depth characteristic.

In some embodiments, at least one of the acquired images corresponds to a diffuse reflection off the object, and wherein the processor is further configured to use the at least one acquired image to measure a hemoglobin level of the object.

In some embodiments, at least one of the acquired images corresponds to a diffuse reflection off the object, and wherein the processor is further configured to use the at least acquired one image to measure a melanin level of the object.

In some embodiments, the processor is configured to use at least one of the acquired images to measure a color characteristic of the object.

In some embodiments, the processor is configured to synchronize the illumination source with a shutter of the camera.

In some embodiments, the camera further comprises a user interface configured to display the multi-layer three dimensional reconstruction of the object.

Another embodiment provides an optical mask, comprising: multiple aperture pairs, wherein each aperture pair is dedicated to a different illumination wavelength, wherein each aperture of each aperture pair is configured to transmit a light pulse from a different one of two optical paths to at least one imaging sensor.

In some embodiments, at least one aperture is disposed with a polarization component.

In some embodiments, each aperture pair has a different size.

In some embodiments, each aperture pair has a different shape.

In some embodiments, one aperture pair shape is round and wherein one aperture pair shape is square, and wherein one aperture pair shape is rectangular.

In some embodiments, each aperture pair is disposed with a color filter corresponding to its dedicated illumination wavelength.

Another embodiment provides a method comprising: controlling an illumination cycle comprising a blue illumination pulse by a blue light source, a green illumination pulse by a green light source, and a red illumination pulse by a red light source; synchronizing a camera shutter with each illumination pulse of the illumination cycle; acquiring a pair of images of an object during each illumination pulse; calculating a depth characteristic of the object using one of the pairs of images acquired from a specular reflection of one of illumination pulses; applying a shift to the pixels of the acquired image as a function of the depth characteristic; measuring a sub-surface quality of the object using any of images acquired from a diffuse reflection of any of the illumination pulses; determining a color characteristic of the object from any of the acquired images; registering the pairs of images received over multiple illumination cycles; and combining the registered pairs of images to create a multi-layer three-dimensional reconstruction of the object.

In some embodiments, the specular reflection corresponds to the blue illumination pulse.

In some embodiments, the diffuse reflection corresponds to any of the red and green illumination pulses.

In some embodiments, the pairs of images are acquired from two regions of a mono sensor.

In some embodiments, one of the images is acquired from polarized light.

In some embodiments, the polarized light corresponds to the blue illumination pulse.

In some embodiments, the polarized light corresponds to any of the green and red illumination pulses.

In some embodiments, the object is skin and the sub-surface quality is a hemoglobin level of the skin.

In some embodiments, the object is skin and the sub-surface quality is a melanin level of the skin.

In some embodiments, the color characteristic is determined from the pairs of images acquired during the blue illumination pulse.

In some embodiments, the color characteristic is determined from one image from each pair of images acquired during each of the blue, green, and red illumination pulses.

In some embodiments, the method further comprises applying to the registered pairs of images any of: an edge enhancement technique, an equalization technique, and an image correlation technique comprising: a) calculating a variance map for each color, b) scaling the variance maps to the same dynamic range, and c) finding the relative positions of detected features to maximize correlation.

In some embodiments, the method further comprises displaying the three-dimensional reconstruction.

Another embodiment provides a method comprising: simultaneously illuminating with a blue illumination pulse by a blue light source, a green illumination pulse by a green light source, and a red illumination pulse by a red light source; synchronizing a camera shutter with the simultaneous illumination pulses; simultaneously acquiring a pair of images for each illumination pulse; calculating a depth characteristic of the object using one of the pairs of images acquired from a specular reflection of one of illumination pulses; applying a shift to the pixels of the acquired image as a function the depth characteristic; measuring a sub-surface quality of the object using any of images acquired from a diffuse reflection of any of the illumination pulses; determining a color characteristic of the object from any of the acquired images; registering the pairs of images received over multiple illumination cycles; and combining the registered pairs of images to create a multi-layer three-dimensional reconstruction of the object.

In some embodiments, the specular reflection corresponds to the blue illumination pulse.

In some embodiments, the diffuse reflection corresponds to any of the red and green illumination pulses.

In some embodiments, the multiple pairs of images are acquired by multiple dedicated regions of a mono sensor.

In some embodiments, the multiple pairs of images are acquired by multiple dedicated sensors.

In some embodiments, one of the images is acquired from polarized light.

In some embodiments, the polarized light corresponds to the blue illumination pulse.

In some embodiments, the polarized light corresponds to any of the green and red illumination pulses.

In some embodiments, the object is skin and the sub-surface quality is a hemoglobin level of the skin.

In some embodiments, the object is skin and the sub-surface quality is a melanin level of the skin.

In some embodiments, the color characteristic is determined from the pairs of images acquired during the blue illumination pulse.

In some embodiments, the color characteristic is determined from one image from each pair of images acquired during each of the blue, green, and red illumination pulses.

The method of claim 38, further comprising applying to the registered pairs of images any of: an edge enhancement technique, an equalization technique, and an image correlation technique comprising: a) calculating a variance map for each color, b) scaling the variance maps to the same dynamic range, and c) finding the relative positions of detected features to maximize correlation.

In some embodiments, the method further comprises displaying the three-dimensional reconstruction.

In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. The figures are listed below.

FIGS. 10A-10D show three cycles for multi-layer image acquisition using the mask of FIG. 9C;

DETAILED DESCRIPTION

A system and method are disclosed herein for 3D image reconstruction. Multiple images may be captured in stereo under varying polarization and color illuminations to obtain different perspective views and characteristics of a three dimensional (3D) object. The imaging system may be used to image a tissue such as skin. Since skin is slightly translucent, illuminating and imaging with varying polarizations and/or wavelengths may allow acquiring images via diffuse reflection, to image characteristics beneath the skin's surface, such as hemoglobin and melanin concentrations. Additionally, imaging in stereo using surface, primarily specular, reflection may provide both color and depth characteristics at the skin's surface indicating scars, lines, and/or other surface details. The multiple images acquired in stereo under varying polarization and color illuminations may be combined to create a multi-layered 3D reconstruction of the skin's surface.

Figure 1A:
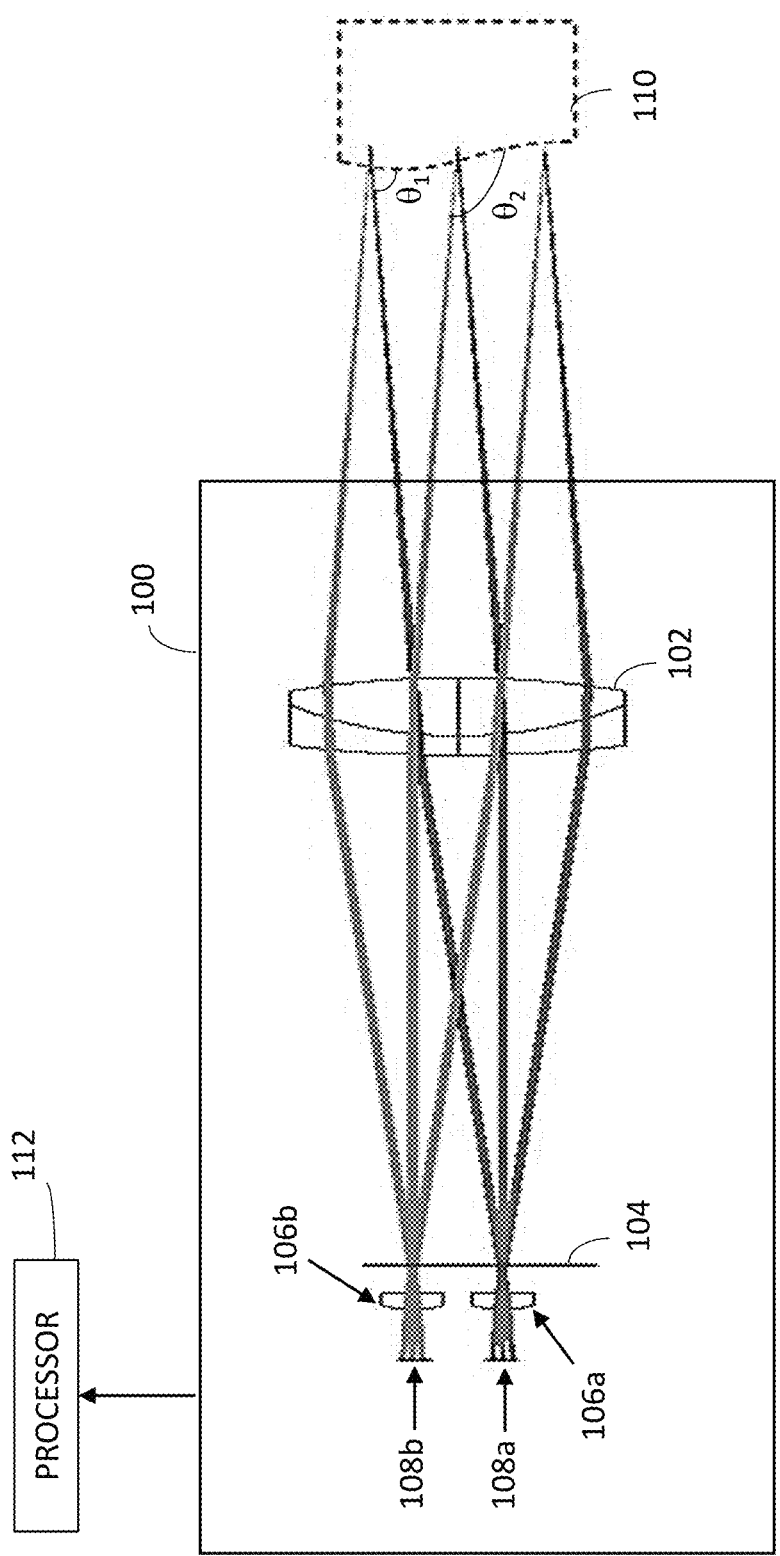
FIGS. 1A-1B, taken together, an optical imaging system in accordance with an embodiment.
Figure 1B:
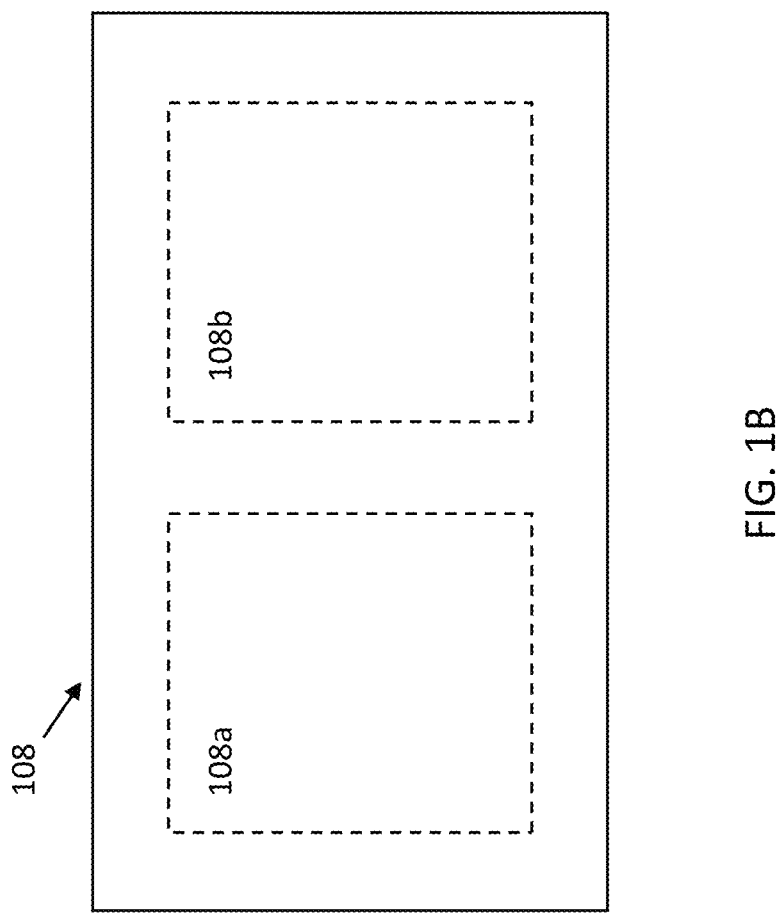

Reference is now made to FIGS. 1A-1B which, taken together, show an optical imaging system in accordance with an embodiment.

An imaging system 100, such as a camera, is provided to capture multiple stereo images of a 3D object 110, such as skin. Camera 100 is provided with a front (objective) lens 102 for collecting light reflected off object 110. The collected light is transmitted through one or more apertures of a mask 104 to a pair of back lenses 106a and 106b, which focus the collected light onto one or more sensors 108a, 108b, such as may comprise any suitable imaging sensor, for example a charged coupled device (CCD) or a complementary metal-oxide semiconductor (CMOS). The captured images may be transmitted to a processor 112 which uses the captured images to reconstruct a 3D image of object 110.

Referring to FIG. 1B, an exemplary view of sensor 108 is shown, according to an embodiment. Sensors 108a, 108b may be implemented as two distinct regions, 108a and 108b of sensor 108. Alternatively, two individual sensors 108a and 108b may be provided for each of the imaging systems.

Camera 100 may constitute two imaging systems, each system comprising one of lenses 106a and 106b and one of sensors 108a and 108b, and sharing common objective 102.

The two imaging systems may allow imaging along separate optical paths, each corresponding to a different one of viewing angles $\theta_1$, $\theta_2$ off of object 110, thereby allowing simultaneous stereo image acquisition. Each of lenses 106a and 106b and sensors 108a and 108b may be dedicated to one of the optical paths. This design may allow the overall length of the imaging systems to be constrained within a predefined size limitation, such as for implementing within a hand-held device. Alternatively, a separate objective (not shown) may be provided for each optical path.

The imaging systems may be telecentric in the sample space of object 110 such as by positioning mask 104 in the rear focal plane of objective 102, allowing to decouple the defocusing and magnification of object 110. Optionally, back lenses 106a and 106b may operate under telecentric conditions such as by positioning mask 104 in the front focal plane of back lenses 106a and 106b. Optionally, the distance between mask 104 to back lenses 106a and 106b may be less than or greater than the focal length of back lenses 106a and 106b to control the imaging properties of the system, for example the distortion. Optionally, the distance between mask 104 to back lenses 106a and 106b may be set to be less than the focal length of back lenses 106a and 106b, such that the chief ray expands at a suitable angle when incident upon the corners of sensors 108a and 108b, to provide an optimum condition for light level uniformity, as is commonly found in many modern image sensors.

The telecentric imaging described thus may allow for uniform scaled imaging, and thus, regions of object 110 positioned either above or below the best-focus plane may be imaged at the same size-scale as regions positioned at the optimum focus. This property may be useful when combining the multiple different captured images by processor 112 for performing the 3D reconstruction of object 110.

Mask 104 may have two or more apertures for transmitting the collected light, each aperture corresponding to a different one of the optical paths. In one implementation, mask 104 includes a pair of round holes to produce the desired F-number (F #) at object 110, such as illustrated in FIG. 1A, where F # is understood to control: the amount of light collected by imaging system 100; the lateral resolution of imaging system 100; and the depth-of-focus of imaging system 100. Optionally, mask 104 provides a high F # to produce a large depth-of-focus by causing the image of a sensor pixel to expand slowly above and below best focus on object 110, as is known in the art.

System 100 may be designed to image object 110 positioned at or near the front focal plane of the front lens such that sensors 108a and 108b and lenses 106a and 106b are operating at infinite conjugates. Thus, light reflected off object 110 at angle $\theta_1$ may be collimated via objective 102 through one aperture of mask 104 and focused via lens 106a onto sensor 108a, and light reflected off sample 110 at angle $\theta_2$ may be collimated via objective 102 through a second aperture of mask 104 and focused via lens 106b onto sensor 108b. In this manner, different points on object 110 imaged at different angles $\theta_1$, $\theta_2$ may be mapped onto different regions of the mask plane and different regions of the sensor plane, comprising a different imaging system for each viewing angle. Similarly, light rays reflecting off a single point of object 110 at different angles $\theta_1$, $\theta_2$ may be parallel when they arrive at mask 104, and transmitted, respectively through the different apertures via back lenses 106a and 106b to sensors 108a and 108b. In this manner, the two imaging systems together allow the simultaneous stereo imaging from multiple different angular views of object 110. Optionally, each viewing angle may be imaged sequentially at sensor 108.

The apertures on mask 104 may be positioned symmetrically opposite about the viewing axis of camera 100, allowing two slightly different views of the 3D surface to be obtained. The disparity Δ between the two different captured views may be computed and used to determine a depth attribute of the imaged 3D surface. The disparity may be computed as the differences between the lateral (X, Y) positions of one or more identified features in the two images. A 3D map of the imaged object may be formed by computing the disparity between each identified feature in the two captured views. The disparity may be computed using any suitable algorithm such as are known in the art of stereoscopy. The depth can be calculated using the following equation:

$$Z = F_1 + \Delta F_1^2/(F_2 b) \quad (1)$$

Where $F_1$ is the front lens (objective) focal length, $F_2$ is the back lens focal length, b is the aperture spacing, Δ is the disparity, and Z is the depth. Values for $F_1$, $F_2$, and b may be selected to set the view angle, magnification, and working distance of camera 100. For example, $F_1$ may range between 60-100 millimeters (mm)±10%, values for $F_2$ may range between 10-35 mm±10%, and values for b may range from 5 to 20 mm±10%.

With the object 110 located in the front focal plane of objective 102, a tradeoff between depth of focus, resolution and light level for round apertures may be described by the following equations:

Lateral Resolution (Rayleigh Criterion, Airy Disk Radius) at object 110 = $1.22\lambda(F_1/D_A)$ (2)

Diffraction-Limited Depth of Focus at object 110 = $\pm 2\lambda(F_1/D_A)^2$ (3)

Light level is proportional to $(D_A/F_1)^2$ (4)

where $D_A$ is the diameter of the aperture and λ is the wavelength. Equations (2) and (3) apply to diffraction-limited imaging systems while equation (4) applies to optical systems in general. Imaging system 100 may be diffraction-limited.

In the event that imaging system 100 is telecentric at object 110, as described above, its field of view (FOV) is limited by the diameter $D_L$ of objective lens 102, focal length $F_1$, and F # of imaging system 100 at the object 110, as follows:

$$FOV \leq D_L - F_1 \times \alpha - F_1/F\# \quad (5),$$

where α is the angle between the right and left viewing angles as measured in radians.

Since a large FOV typically requires a large objective, resulting in a heavy and bulky optical system, the FOV may be constrained to allow camera 100 to have a size and weight that are suitable for a handheld device. To compensate for a smaller FOV, object 110 may be scanned to capture many consecutive image pairs. Equation (1) may be applied to each of the image pairs acquired using the stereo imaging system above, to calculate the depth attribute, or a 3D point cloud, for each image pair. A registration algorithm may be used to add all the calculated 3D point clouds together and form a large 3D point cloud representing the scanned region.

Any noise of a single 3D point cloud may be accumulated in the registration process, resulting in a significant noise level for the large 3D point cloud. To limit the sensitivity to noise, camera 100 may be designed such that the angle α between the left and right images (the image pairs acquired in stereo), may be substantially small, such as ~6°. Alternatively, the angle α between the left and right images may range between 5.5° and 6.5°, or 5° and 7°, or 4° and 8° or 3° and 9°. Thus, the features in the left image and right image may be very similar, allowing a high degree of accuracy in discerning features along the lateral, x, and vertical, y axes. However, there may remain a non-negligible distortion along the depth, z axis.

Figure 2A:
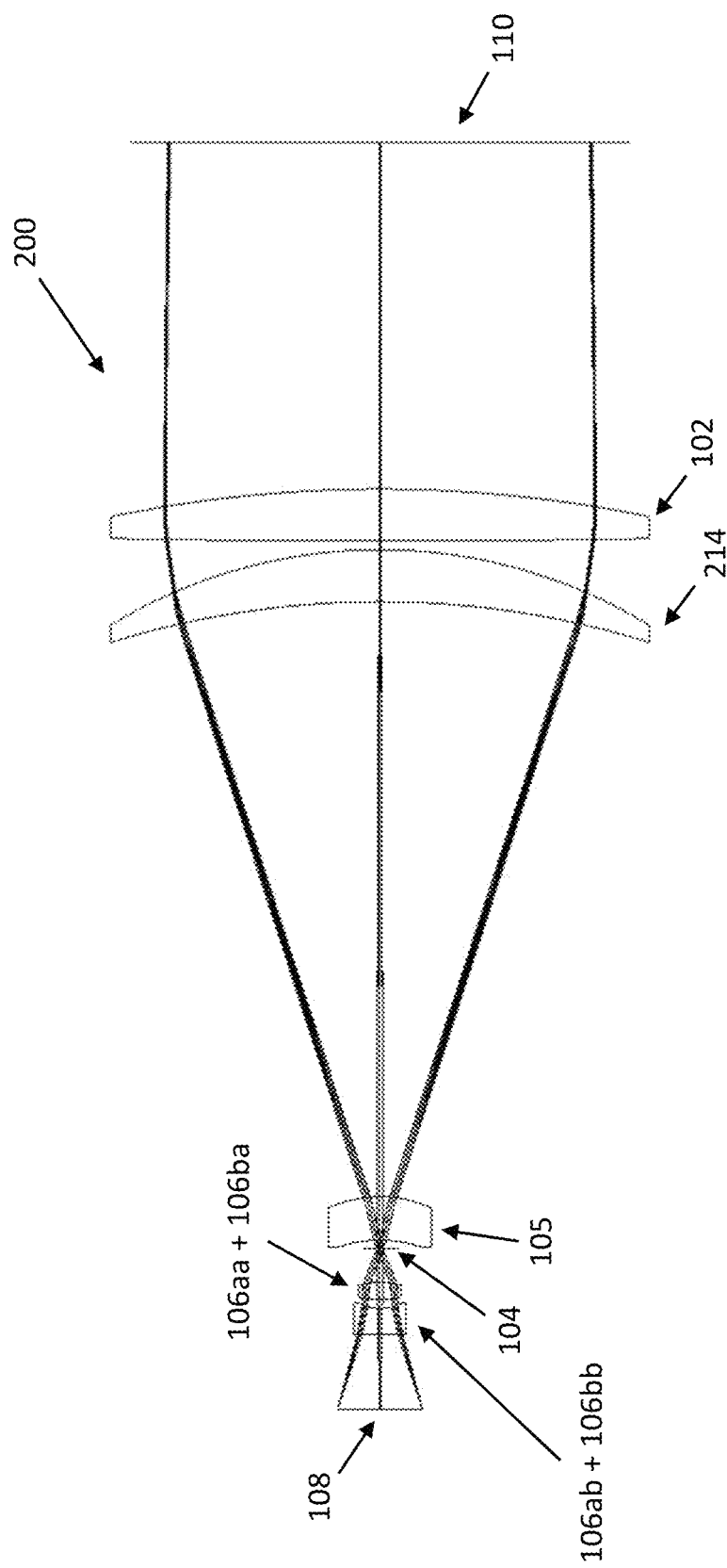
FIGS. 2A-2B illustrate an optical imaging system in accordance with another embodiment.
Figure 2B:
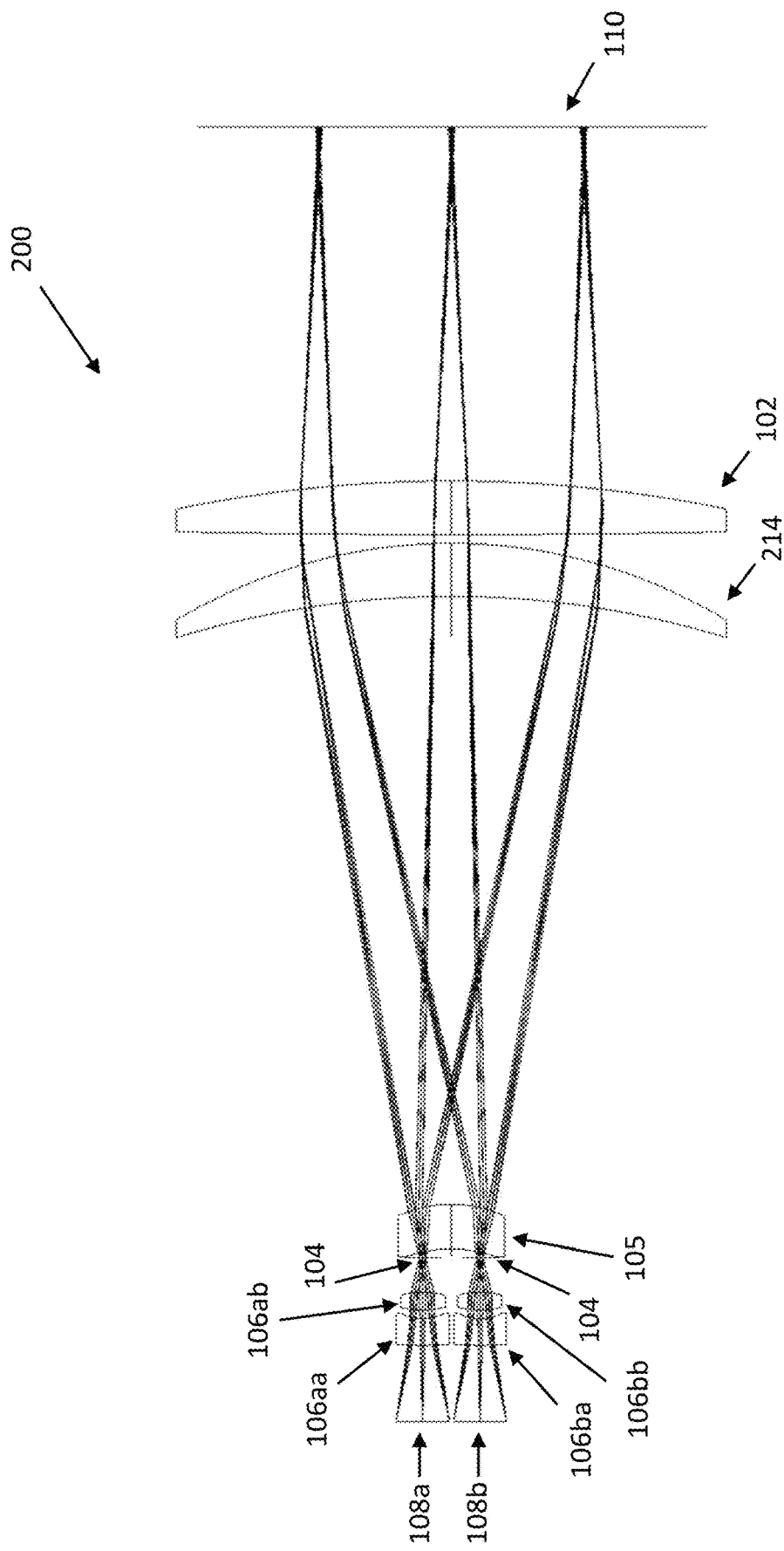

Reference is now made to FIGS. 2A-2B which illustrate perpendicular views of an optical imaging system 200 designed to achieve an expanded field-of-view while maintaining careful control of imaging performance, in particular optical distortion, in accordance with another embodiment.

Distortion is an optical aberration which incorrectly maps points on the object to the image. This incorrect mapping of points may have a substantial effect on 3D point clouds. Following Eq. (1), the relationship dz between z (depth) and disparity (Δ) in a system with a relatively small angle between left and right images, such as ~6° is dz~10*Δ, where the disparity is calculated in the image plane. In such a system, even very low distortion, such as tenths of a percent, may have a non-negligible effect on the large 3D point cloud. To avoid such errors, telecentric optical imaging system 200 may capture images with very low distortion, such as <0.5%.

The distortion in an optical system is typically an inherent attribute of the optical design, and may vary with the depth; when in focus, an optical system may acquire images with very low distortion, however images acquired far from focus may suffer from high distortion. To address this problem, the lenses 102, 214, 105, and 106 (where lens 106 can be a sequential array of multiple lenses which allow, together, a greater degree of control over various imaging properties, such as distortion) work together to minimize the distortion of the optical system in-focus, and also to cause the distortion to change very gradually with defocus, resulting in relatively low distortion along the entire depth of focus. By reducing the distortion for each captured image, the cumulative error for the 3D point cloud resulting from the registration may be reduced significantly.

The system of FIG. 2A and FIG. 2B is substantially similar to that of FIGS. 1A-1B having two imaging systems for two optical paths each corresponding to a different viewing angle of object 110, with the notable differences that: First, instead of one front lens 102 as in the system of FIG. 1A, there are three lenses (102, 214 and 105) in the system of FIGS. 2A-2B. Second, instead of one back lens 106 in each optical path of FIGS. 1A-1B (namely, lenses 106a and 106b), there is a pair of back lenses for each optical path in FIGS. 1A-1B, namely, back lenses 106aa and 106ab in one optical path, and back lenses 106ba and 106bb in the other optical path. These back lenses, together with the front lenses, allow control of the distortion. Light reflected off object 110 in two separate optical paths is collected by the set of three front lenses (102, 214 and 105). The light of each optical path is collimated onto a different aperture of mask 104 and transmitted through the apertures via back lens pairs 106aa+106ab and 106ba+106bb onto sensors 108a and 108b, respectively.

The overall length of the system 200 of FIG. 2A may range from 100 to 130 mm. In one embodiment, the overall length is approximately 120 mm±10%. The maximum diameter of system 200 may range from 60 to 80 mm, and in one embodiment may be approximately 70 mm±10%. The average distortion may range from 0.4% to 0.6% and in one embodiment may be approximately 0.5%. The FOV may range from 60×25 mm to 60×35 mm, and in one embodiment, may be approximately 60×30 mm±10%. The depth of focus may range from ±15 mm to ±25 mm and in one embodiment, may be approximately ±25 mm±10%. The depth of focus as described here takes into account the geometric optics imaging behavior of system 200 as well as the sampling of sensor 108, and may be different than the diffraction-limited depth of focus as defined above in equation (3). The 3D resolution may range from 80 to 100 microns, and in one embodiment, may be 100 microns±10%.

Figure 3:
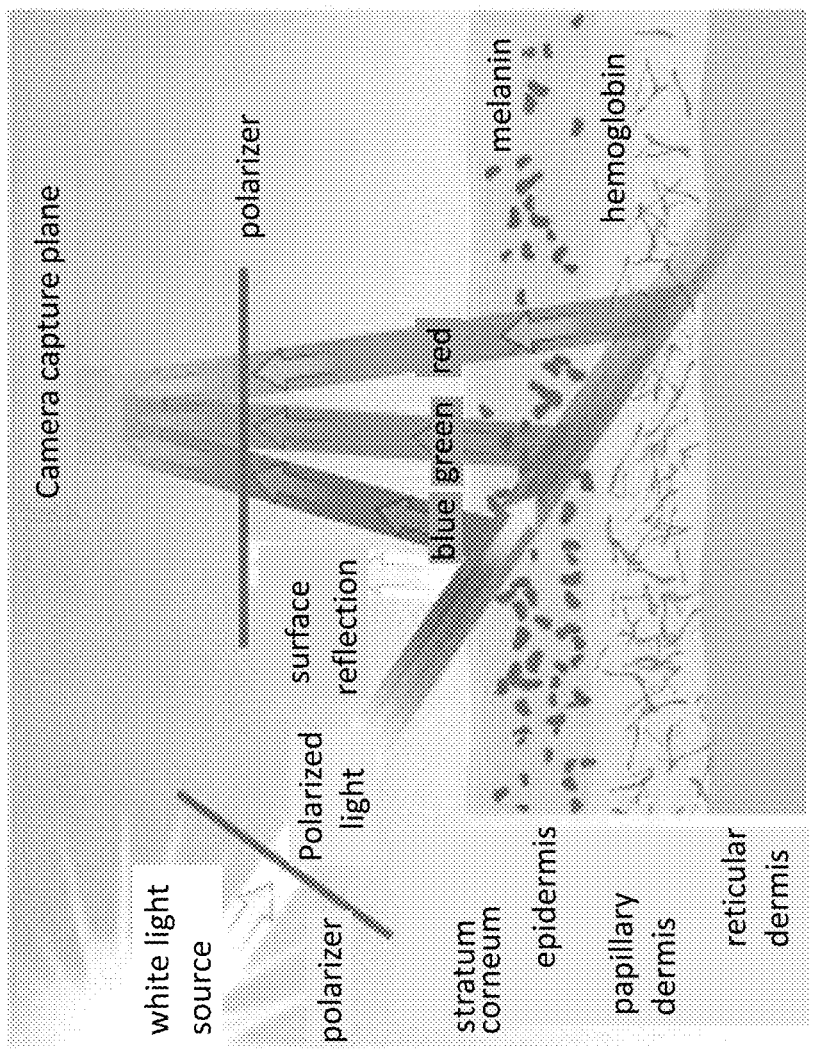
FIG. 3 illustrates reflective properties of human skin.

Reference is now made to FIG. 3 which illustrates reflective properties of human skin, and which may be leveraged in order to select one or more spectral bandwidths that allow acquiring images detailing various skin features. The spectral bandwidth can be controlled in the illumination path, the imaging path, or a combination. Skin typically absorbs light in a wavelength dependent manner with the penetration depth generally increasing with the wavelength in the visible spectrum. Thus, red wavelengths are typically absorbed deeper into skin tissue than green wavelengths, which are absorbed deeper than the blue range of the visible spectrum, a property which may affect their respective surface and sub-surface reflection and scattering from the skin.

Thus, it may be appreciated that acquiring multiple images of the skin illuminated with different wavelengths having different specular and diffuse and surface and sub-surface reflective properties may allow measurement of different skin characteristics both from the skin's surface and beneath. For example, the longer wavelength ranges that penetrate beneath the skin, such as the red and green ranges of the visible spectrum, may be used to detect melanin and hemoglobin levels, and the surface reflective properties of blue light may be used to detect surface features of the skin. Multiple images may be acquired under illumination by different wavelengths using the system and method disclosed herein. These images may be combined with the 3D map created above to produce a multi-layer 3D reconstruction of the skin.

Optionally, a mask, such as mask 104 illustrated in FIGS. 1A, 2A, and 2B, may be provided with multiple aperture pairs, each pair dedicated to a different wavelength range, to separately acquire multi-spectral images of the skin, each indicating different skin characteristics. Details of mask 104 are described in greater detail below with respect to FIGS. 9A-9D. Each aperture of each aperture pair may correspond to a different one of the two viewing systems, allowing for multi-spectral stereo image acquisition.

Figure 4A:
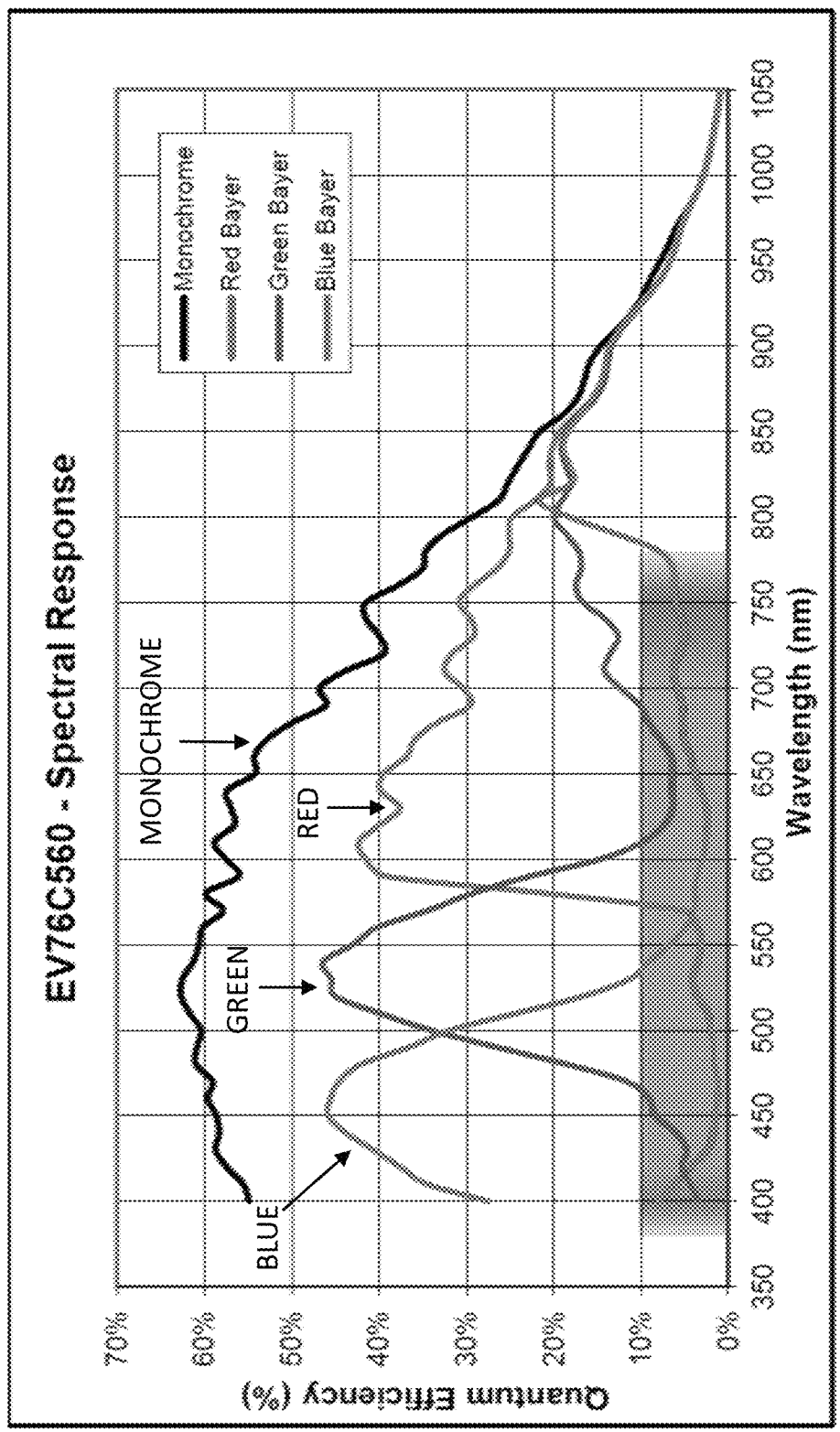
FIG. 4A shows the spectral response of various optical Bayer filters.

Reference is now made to FIG. 4A which shows the spectral response of various optical Bayer filters. In one embodiment, such filters may be disposed with mask 104 of FIGS. 1A, 2A-2B, and 9A-9D when illuminating a sample using a white light source, to detect surface and sub-surface reflections under varying wavelengths. As indicated in FIG. 4A, Bayer filters typically have a very large bandwidth, in the order of a full-width-at-half-maximum (FWHM) bandwidth of 100 nm. Thus, a Bayer filter dedicated to transmitting blue light may transmit a substantial amount of green light that penetrated to the epidermis layer. Additionally, since typical Bayer filters have low transmission, and the blue light portion of the white LED spectrum may be relatively weak, collecting a sufficient amount of blue light for imaging requires a high intensity white light source.

Figure 4B:
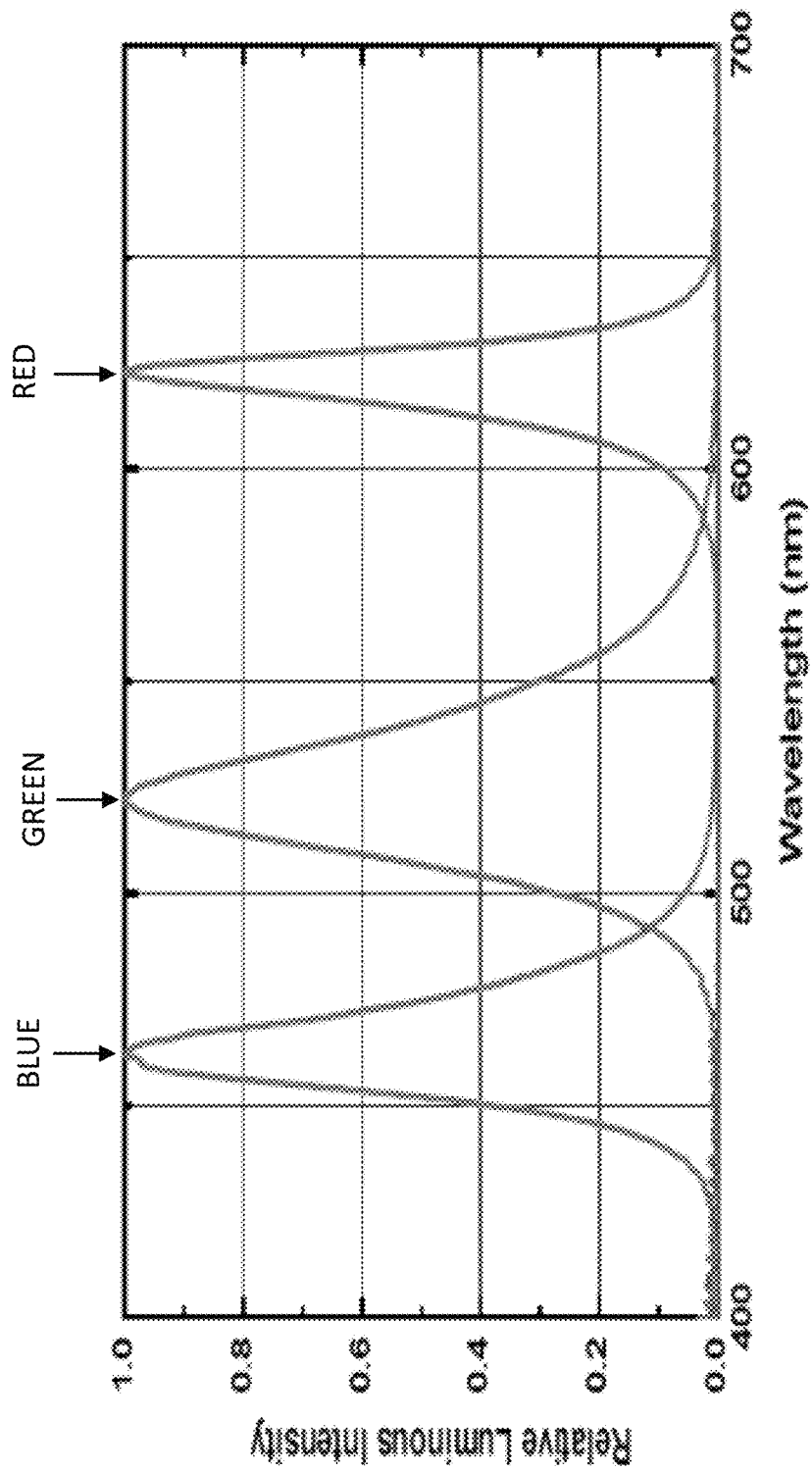
FIG. 4B shows the illumination bandwidths of various color light emitting diodes (LEDs)

Referring to FIG. 4B, the illumination bandwidths of several color LEDs is shown, each having a FWHM bandwidth in the range of 10 nm to 30 nm. It may be appreciated the bandwidth for each light source is substantially narrower than the bandwidth allowed using the Bayer filters of FIG. 4A. Thus, it may be appreciated that illuminating with multiple color LEDs each having a narrow bandwidth, such as in the range of 10 nm, may allow detecting each wavelength range separately, precluding the collection of green light with blue light.

Typically, color sensors allocate one quarter of the pixels for capturing blue light, and thus, sampling, or digital resolution for blue wavelengths is one half of the sensor resolution in each lateral direction X and Y. Thus, in order to acquire a sufficient amount of light to perform high resolution imaging, sensor 108 may be a mono sensor that sequentially acquires images under illumination by multiple different monochromatic LEDs. Three monochromatic LEDs, corresponding to red, green, and blue wavelength ranges, may sequentially illuminate sample 110, allowing mono sensor 108 to separately detect each individually reflected wavelength range. Processor 112 may synchronize the illumination cycle of the LEDs with the shutter of camera 100 or 200, and may sort the detected images according to their illumination wavelength range. The term "shutter" refers to either a mechanical (leaf, diaphragm, etc.) shutter, or to electronic shutter functionality of the image sensor itself, which electronically "shades" sensor cells, as known in the art.

Alternatively, sensor 108 may be divided into different regions, each region allocated to detect a different one of the wavelength ranges. Thus, sensor 108 may have a region allocated for acquiring images of the tissue under blue, red, and green illumination, accordingly. This configuration allows simultaneously illuminating the tissue with all three wavelength ranges, and capturing individual images for each illuminating wavelength range.

Considerations for designing the system for either sequential or simultaneous illumination and detection may include constraints on the size of the detector: a small detector 108 may be more suited for sequential illumination-detection, whereas a larger detector 108 may be more suited for simultaneous illumination-detection, having a greater number of pixels and/or detection area that can be divided and allocated among the different wavelength ranges while providing sufficient resolution.

Additionally, illumination-shutter synchronization, in either of the sequential or simultaneous illumination regimes, may be performed with illumination pulses which are substantially equal in length to shutter opening times, or with continuous illumination which spans temporally over multiple shutter openings.

Figure 5A:
FIGS. 5A-5C show multiple images of human skin captured using varying illumination and sensors.
Figure 5B:
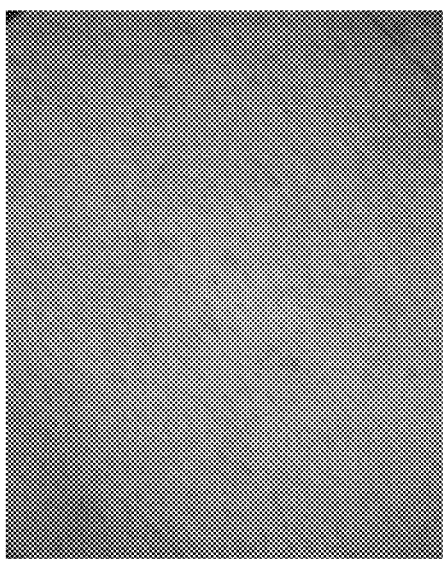
Figure 5C:
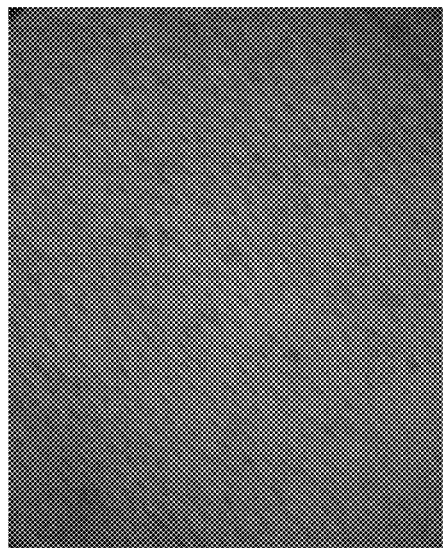

Reference is now made to FIGS. 5A-5C which show images of human skin captured using varying illumination and sensors. FIG. 5A shows a skin sample illuminated using a blue LED having a full-width-at-half-maximum (FWHM) bandwidth of approximately 20 nm and detected using a mono sensor. FIG. 5B shows the same skin sample illuminated using white illumination and detected using a color sensor. FIG. 5C shows an image created from the blue pixels of the FIG. 5B. It may be appreciated that significantly more details are evident in FIG. 5A than in any of FIGS. 5B-5C. Thus, images may be acquired of the skin while illuminating with a blue LED. These images may be used for 3D reconstruction.

Figure 6:
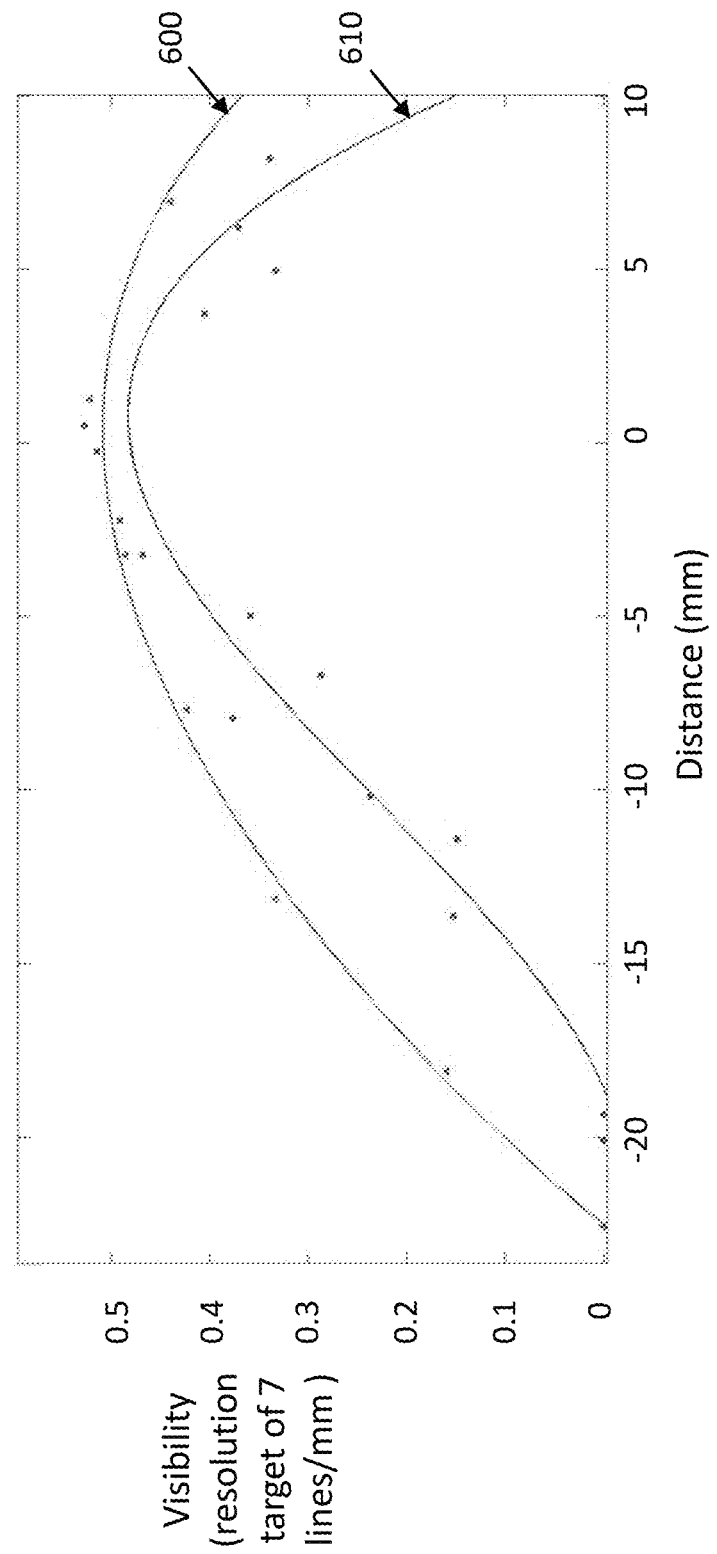
FIG. 6 shows visibility as a function of distance from a camera using a mono sensor and color sensor.

Reference is now made to FIG. 6 which shows visibility measured with a resolution target of 7 lines/millimeter (mm) as a function of distance from camera. Visibility is defined as (maximum intensity−minimum intensity)/(maximum intensity+minimum intensity). FIG. 6 shows visibility of a standard resolution target captured using a mono sensor (curve 600) and a color sensor (curve 610) as measured at varying distances (in mm) from the camera. It may be appreciated that the visibility using a mono sensor, indicated by curve 600, is consistently higher and covers a broader distance range than with the color sensor, indicated by curve 610.

Polarization describes the electric field orientation with respect to the meridional plane in an optical system, where S polarization indicates a perpendicular orientation and P represents a parallel orientation. Illuminating with polarized light may provide additional information about the skin. When the LEDs are oriented off-axis of the imaging path, their light may be S or P polarized using one or more polarizers, independently of the imaging path.

Different combinations of parallel and/or crossed (orthogonal) polarizer pairs may be provided in the illumination and imaging paths: a linear polarization component, typically referred to as the "polarizer" may be provided with the LED to polarize the emitted light and illuminate the surface with the polarized light, and a complementary linear polarization component, typically referred to as the "analyzer" (parallel, crossed, or at another orientation to the polarizer) may be provided at one or more of the apertures of mask 104, accordingly. Alternatively, the "analyzer" may be provided at the collecting lens 102 or another suitable location in the optical path. Additionally, or alternatively, other polarization components, for example wave-plates and prisms may be provided in the illumination and/or imaging paths to achieved desired effects.

Optionally, the surface may be measured under four different types of illumination and imaging conditions:

1) Non-polarized, or randomly polarized light, by omitting polarization components from the optical path,
2) Parallel polarization in the illumination and imaging paths by providing two polarizers that are parallel to each other: a linear polarizer at one or more of LEDs 122 and a linear polarizer along the imaging path, such as at mask 104,
3) Perpendicular polarization in the illumination and imaging paths by providing two linear polarizers that are perpendicular to each other, one linear polarizer at one or more of LEDs 122 and the other linear polarizer along the imaging path, such as at mask 104, and
4) Arbitrary angle between the polarization of the illumination path and the polarization of the imaging path, allowing a combination of parallel and perpendicular polarization conditions to be collected simultaneously. The ratio between the parallel and perpendicular polarization conditions may be set by the relative rotation angles of the linear polarizers in the illumination and imaging paths. The ratio may also be made adjustable to optimize the system for specific requirements or conditions (skin tone, color, moisture, etc.)

Figure 7C:
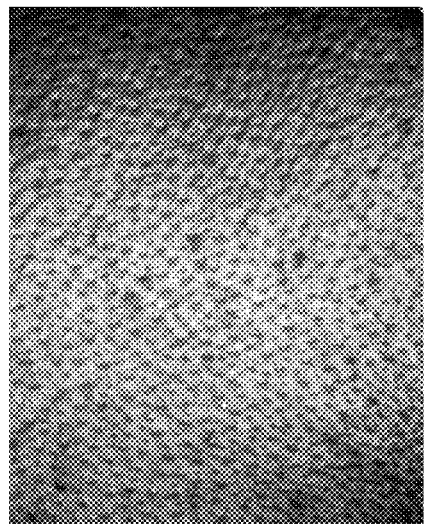
FIGS. 7A-7C show images of human skin captured using a mono sensor under blue illumination with no polarization, parallel polarization, and cross-polarization.
Figure 7B:
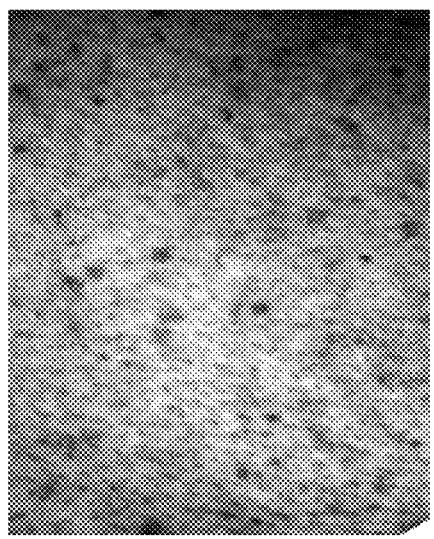
Figure 7A:
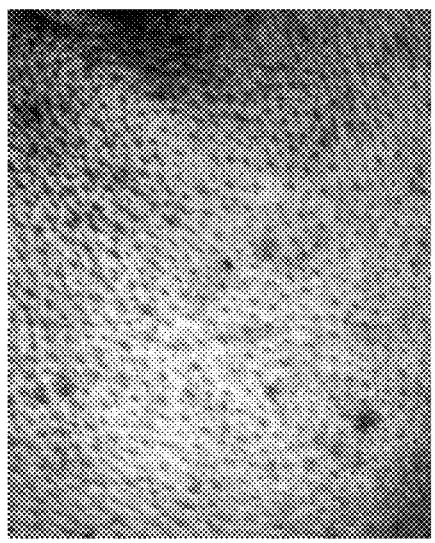

Referring to FIGS. 7A-7C, images of human skin captured using a mono sensor under blue illumination with no polarizers (FIG. 7A), mono sensor under blue illumination with cross polarizers on the LEDs and imaging path (FIG. 7B), and mono sensor under blue illumination and parallel polarizers on the LEDs and imaging path (FIG. 7C), are shown. It may be appreciated that under illumination by blue light with parallel polarizers, the 3D texture of the skin surface as indicated by the skin pores is discernible (FIG. 7B), whereas with the crossed polarizers (FIG. 7C) only the pigmentation is discernible. In FIG. 7A, without the polarizers, both the skin surface and pigmentation are discernible.

When calculating 3D disparity maps from 2D images, the disparity is calculated between features present in each of the image pairs acquired in stereo. Pigmentation features may provide more accurate information for depth resolution, since textured skin features such as pores may appear differently under varying lighting conditions. Since pigmentation is less dependent on lighting conditions, images captured using blue light illumination with a mono sensor and no polarizer may be used for 3D measurements.

Since melanin and hemoglobin are found under the surface of the skin, imaging using light free of surface reflection together with crossed polarizers may provide more accurate data for measuring levels of these compounds.

Figure 8A:
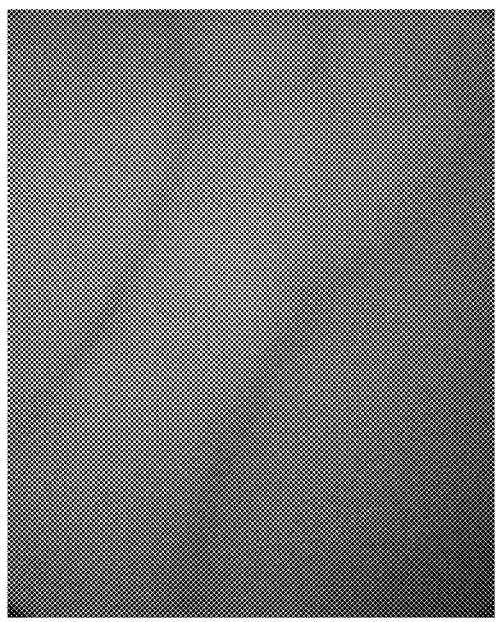
FIGS. 8A-8B show images of human skin captured using parallel polarizers and crossed polarizers, respectively.
Figure 8B:
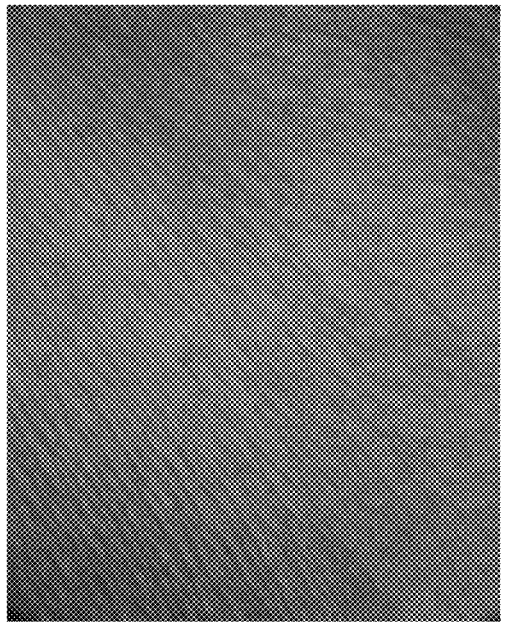
Figure 8C:
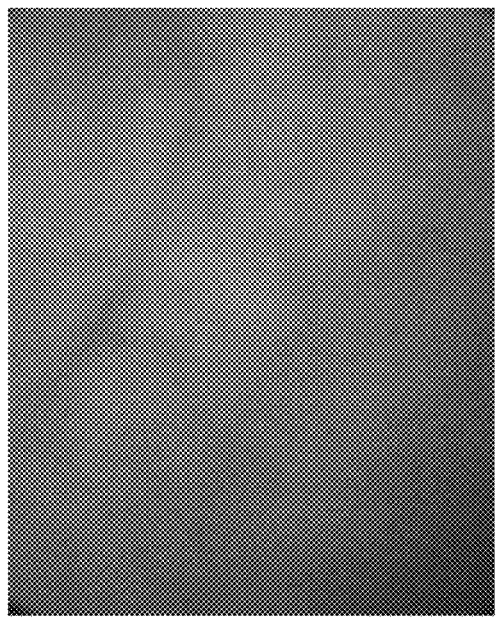
FIGS. 8C and 8D show images of human skin captured under green and red illumination, respectively, with cross polarizers.
Figure 8D:
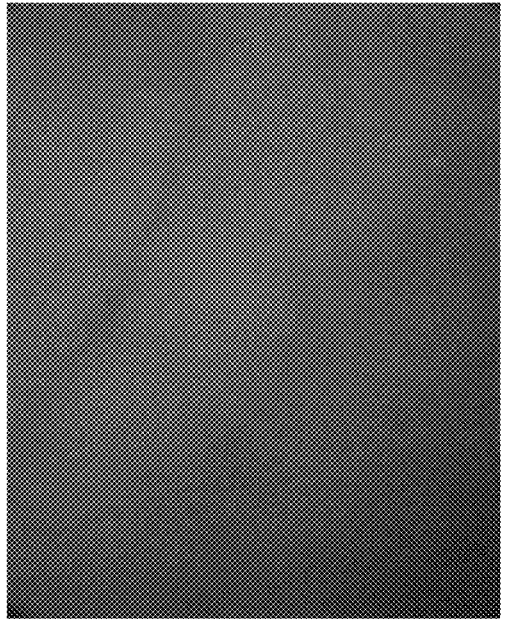

Referring to FIGS. 8A-8D, images of a human skin sample captured using parallel polarizers and crossed polarizers, respectively, are shown. FIG. 8A shows an image of the human skin sample captured using parallel polarizers that collect light reflected from the skin surface, and FIG. 8B shows an image of the same skin sample captured using crossed polarizers that collect light that penetrated into the skin. FIGS. 8C and 8D show images of the same skin sample captured under green and red illumination, respectively, with cross polarizers. It may be appreciated that use of the crossed polarizers enable the detection of light scattered at much deeper layers of the skin.

Thus, acquiring images of the skin using polarized light of different wavelengths may provide measurements of additional skin characteristics. Such images may be combined with the multi-layer 3D reconstruction produced above as an additional layer.

Figure 9A:
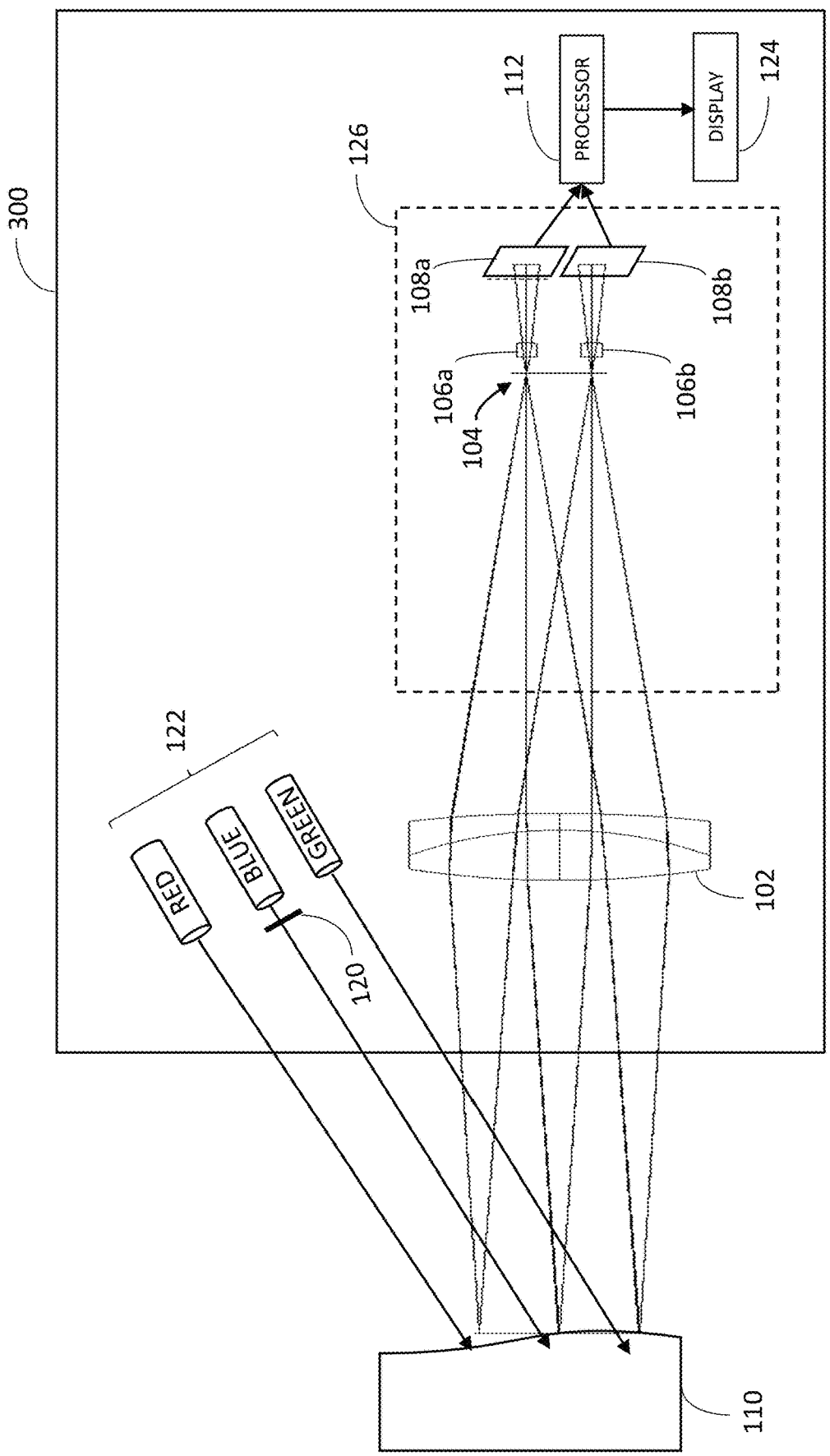
FIGS. 9A-9D, taken together, illustrate a system for multi-layer image acquisition for a 3D reconstruction of an object in accordance with an embodiment.
Figure 9C:
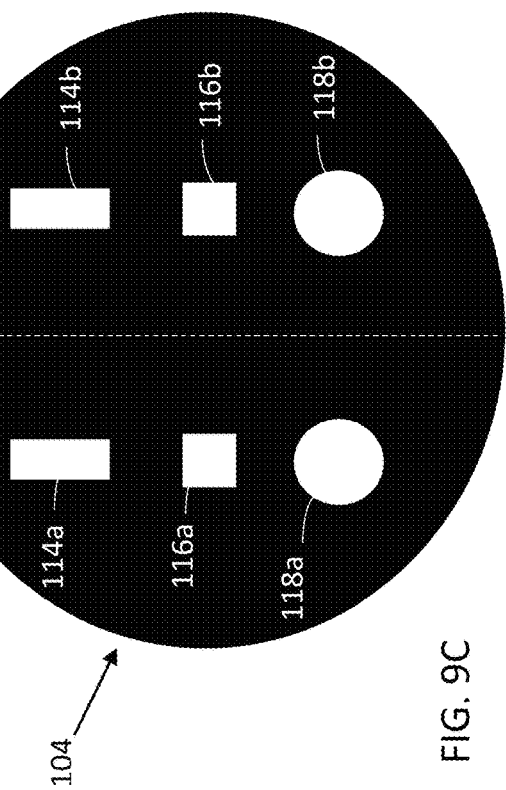
Figure 9B:
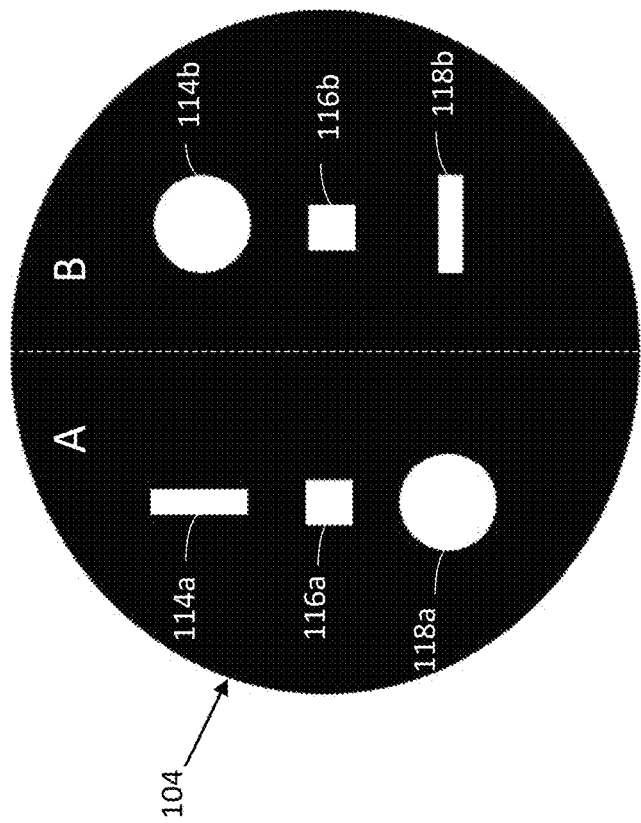
Figure 9D:
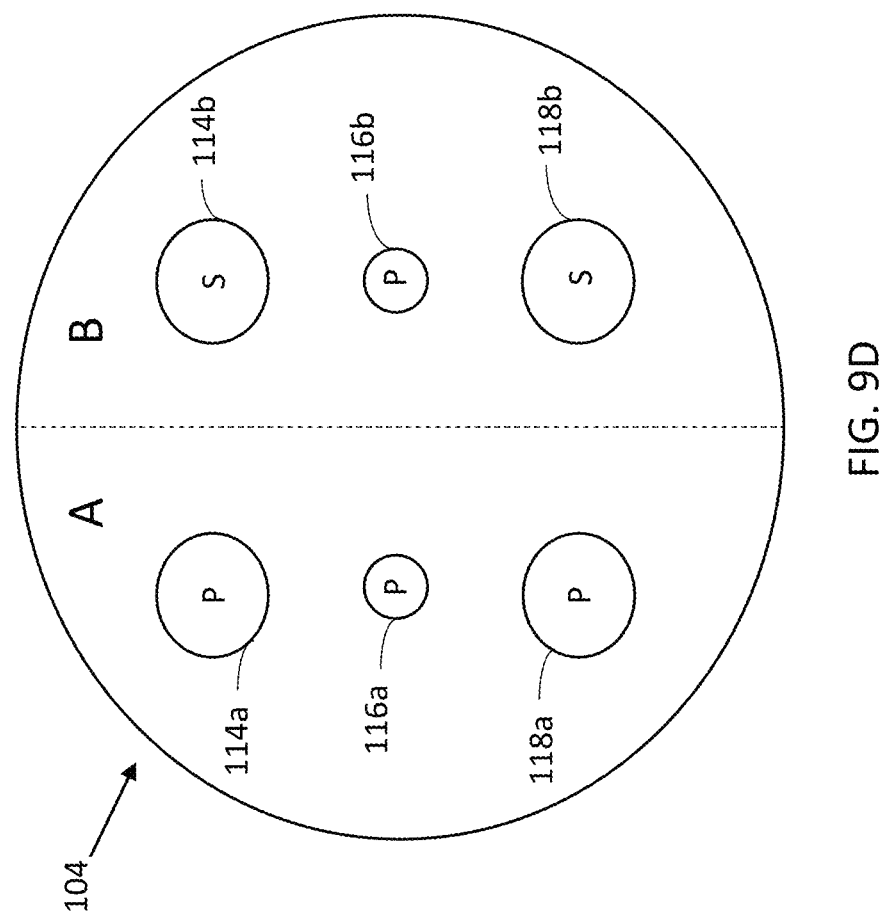

Reference is now made to FIGS. 9A-9D which, taken together, illustrate a system for multi-layer image acquisition for 3D reconstruction of an object. The system 300 of FIG. 9A is substantially similar to the system of FIGS. 1A-1B and 2A-2B having two viewing systems each comprising a different optical path corresponding to a different viewing angle of an object, with the notable difference that an illumination source 122 includes three individual light sources, such as red, green, blue light emitting diodes (LEDs). An optical apparatus 126 is provided to operate with the multiple illumination sources 122. Apparatus 126 includes mask 104, one or more back lenses, such as lenses 106a and 106b, and one or more detectors, such as detectors 108a and 108b. FIG. 9A shows a profile view of mask 104 and FIGS. 9B-9D show exemplary front views of mask 104 having multiple apertures for guiding light emitted by LEDs 122.

The wavelength of the blue LED may range from 450 nm to 460 nm, or 455 nm to 465 nm, or 460 nm to 470 nm, or 465 nm to 475 nm, or 470 nm to 480 nm, or 475 nm to 485 nm, or 480 nm to 490 nm, or 485 nm to 495 nm, or 450 nm to 465 nm, or 460 nm to 475 nm or 470 nm to 485 nm or 480 nm to 495 nm, or 450 nm to 470 nm, or 460 nm to 480 nm, or 470 nm to 490 nm, or 475 nm to 495 nm.

The wavelength of the green LED may range from 495 nm to 505 nm, or 505 nm to 515 nm, or 515 nm to 525 nm, or 525 nm to 535 nm, or 535 nm to 545 nm, or 545 nm to 555 nm, or 555 nm to 565 nm, or 560 nm to 570 nm, or 495 nm to 510 nm, or 510 nm to 525 nm, or 525 nm to 540 nm, or 540 to 555 nm, or 555 nm to 570 nm, or 495 nm to 515 nm, or 515 nm to 535 nm, or 535 nm to 555 nm.

The wavelength of the red LED may range from 620 nm to 630 nm, or 630 nm to 640 nm, or 640 nm to 650 nm, or 650 nm to 660 nm, or 660 nm to 670 nm, or 670 nm to 680 nm, or 680 nm to 690 nm, or 690 nm to 700 nm, or 700 nm to 710 nm, or 710 nm to 720 nm, or 720 nm to 730 nm, or 730 nm to 740 nm, or 740 nm to 750 nm, or 620 nm to 635 nm, or 635 nm to 650 nm, or 650 nm to 665 nm, or 665 nm to 680 nm, or 680 nm to 695 nm, or 695 nm to 710 nm, or 710 nm to 725 nm, or 725 nm to 740 nm, or 735 nm to 750 nm, or 620 nm to 640 nm, or 640 nm to 660 nm, or 660 nm to 680 nm, or 680 nm to 700 nm, or 700 nm to 720 nm, or 720 nm to 740 nm, or 730 nm to 750 nm.

Mask 104 may be disposed with multiple different apertures pairs 114, 116, and 118, optionally having varying shapes and/or sizes. Mask 104 and or LEDs 122 may be positioned within the camera 300 such that each aperture pair 114, 116, and 118 is dedicated to a different one of LEDs 122 and/or light polarization to capture optical properties, including but not limited to specular and diffuse reflection, surface and sub-surface scattering, and absorption characteristics of sample 110. Optionally, each of aperture pairs 114, 116, and 118 may be optically aligned with a different one of LEDs 122. For example, each of apertures pairs 114, 116, and 118 may be provided with a different color filter such that, for example, aperture pair 114 may be dedicated to transmitting red wavelengths, aperture pair 116 may be dedicated to transmitting blue wavelengths, and aperture pair 118 may be dedicated to transmitting green wavelengths. This may allow simultaneous illumination of sample 110 with the three LEDs 122 and capture of multiple images of sample 110, an image for each LED 122 and for each of the two imaging systems, at different dedicated sensors 108 or regions thereof. Alternatively, if such color filters are used, the illumination may be white-only, instead or red, blue, and green LEDs.

Optionally, any of the apertures of mask 104 may be disposed with a polarization component, such as an analyzer or retarder, complementing a polarization component configured with one of more of LEDs 122 allowing to detect one or more skin characteristics sensitive to polarization. By detecting an image of surface 110 separately via each aperture, multiple stereo images of surface 110 may be acquired indicating features sensitive to different optical attributes, such as the illumination wavelength, polarization, aperture shape, and the like.

Each side of mask 104, A and B, delineated by a dashed line for illustrative purposes, may correspond to a different one of the two imaging systems, and thus each aperture of each of pairs 114, 116, and 118 positioned on the respective sides of mask 104 may be dedicated to transmitting a light pulse along one of the two optical paths corresponding to one of viewing angles $\theta_1$, $\theta_2$, allowing to determine the depth characteristics indicating the 3D texture of object 110. Thus, light from each of LEDs 122 reflecting off object 110 at the two different viewing angles $\theta_1$, $\theta_2$ may be transmitted via each of the viewing systems and the respective dedicated apertures 114a, 116a, and 118a disposed on side A and apertures 114b, 116b, and 118b disposed on side B of mask 104 to detectors 108a and 108b or dedicated regions of a monosensor 108, allowing for multi-spectral stereo image acquisition. Processor 112 may combine the acquired images pairs to produce a multi-layer 3D reconstruction of object 110. Processor 112 may display the multi-layer 3D reconstruction on a user display 124.

Referring to FIG. 9B, an implementation for a multi-aperture mask 104 is shown, having aperture pairs 114, 116, and 118 comprising apertures 114a, 114b, 116a, 116b and 118a, 118b, disposed on sides A and B, respectively, allowing for multi-layer image acquisition. Each of the apertures and/or the aperture pairs 114, 116, and 118 may be of a different size and/or geometric shape. The aperture diameters and geometric shapes may vary in accordance with the required resolution, light intensity, and depth of focus. The apertures of each pair may be positioned symmetrically opposite to each other about vertical and horizontal diameters of mask 104, and about the viewing axis of system 300. Each of the two optical paths may be directed to a different aperture of each pair, allowing stereo image acquisition in accordance with the attributes designated for each aperture pair.

Referring to FIG. 9C, mask 104 is shown as substantially similar to mask 104 of FIG. 9B, with the noted difference that the apertures of each pair have a matching shape resulting in a symmetry about the diameter of mask 104. In this example, apertures 114a and 114b are longitudinally disposed rectangular slits, apertures 116a and 116b are squares, and apertures 118a and 118b are round, however this is not meant to be limiting and other shapes, or arrangements may be used.

For stereo vision two identical or similar apertures may be provided, separated to view surface 110 at angles that differ at least by approximately 6°. To provide for a sufficiently large area on the two regions of sensor 108, or sensors 108a and 108b for 3D imaging, at least the two central positioned apertures 116a, and 116b of the mask for 3D may be used. The other apertures (114a, 114b, 118a, and 118b) may be used separately with each aperture optionally having different size, and shape. The size and shape of the apertures determines the resolution, depth of focus and light level according to Eq. 2-4. Round apertures give the same resolution in both directions, the larger the aperture the higher the resolution and light level but the lower the depth of focus. Other shapes may be used to capture features that require different resolutions in different directions. For example, to detect 2D and/or 3D features on the skin, such as wrinkles, stretch marks, etc., that require high spatial resolution in one direction and lower spatial resolution in the other direction, an aperture that is narrow in one direction and wide on the other direction may be used, such as may have an elliptical or rectangle shape. Detecting the light from multiple different directions may also enable a better reconstruction of the 3D map of object 110.

Light rays passing through the apertures positioned on one side of mask 104 (i.e. the side marked 'A') shown as apertures 114a, 116a, and 118a, may be directed towards sensor 108a positioned on the left side of the viewing axis, while light rays passing through apertures 114b, 116b, and 118b positioned on the side of mask 104 marked 'B' may be directed to sensor 108b, positioned on the right side of the viewing axis. Light passing through the upper and lower apertures 114a, 114b and 118a, 118b may be focused onto sensors 108a and 108b at different angles than light passing the centrally positioned apertures 116a and 116b. The light passing through mask 104 may be detected are dedicated regions of a single sensor 108 or at one or more smaller, dedicated sensors, described in greater detail below.

Reference is now made to FIG. 9D which illustrates an exemplary implementation of mask 104 disposed with one or more polarization components. Surface 110 may be illuminated via one or more light sources 122 disposed with one or more polarization components, and one or more apertures dedicated to the LED with the polarization component may be disposed with a complementary polarization component. These paired polarization components may be parallel or crossed (orthogonal) with respect to each other, with 'S' and 'P' as defined above.

Thus, for aperture pair 114 dedicated to red light, one aperture (114a) may be have a parallel polarization component (P) and the other aperture (114b) may have a perpendicular polarization component (S). For aperture pair 116 dedicated to blue light, both apertures (116a, 116b) may have a parallel polarization component (P). For aperture pair 118 dedicated to green light, one aperture (118a) may be have a parallel polarization component (P) and the other aperture (118b) may have a perpendicular polarization component (S). However, this implementation is meant to be illustrative only, and is not meant to be limiting.

Alternatively, other polarization components may be used, such as quarter-wave and half-wave plates for the different color/aperture-size/shape apertures of mask 104.

Optionally, the polarization for each aperture may be as indicated in FIG. 9D: apertures 114a, 116a, 118a, and 114b, 116b, and 118b may have polarizers that are parallel or crossed (orthogonal) compared to the polarizers on the LED's (120 for example) or alternatively not have polarizers at all.

Since blue light does not penetrate very deeply into the skin, blue light may be used for collecting light from the surface of object 110. Blue light is primarily reflected from the skin's surface as both specular and diffuse reflectance. Since the imaging system disclosed herein collects a small angular range due to the high F/#, and the diffuse reflection is spread into a relatively large angular range, and thus a relatively small amount of light from each LED is transmitted through the aperture, primarily comprising specular reflection. Accordingly, blue light source 122 may be provided with a polarizer 120 and middle apertures 116a and 116b dedicated to transmitting the blue light may be provided with a parallel polarizer (not shown), such as a polarized coating, allowing the surface reflection of the polarized blue light to be transmitted via dedicated aperture pair 116 to detector 108. These images acquired using blue light may be used by processor 112 to measure the depth characteristics of skin surface 110.

Conversely, light that undergoes diffuse reflection or scattering may change its polarization state. Thus, one or more perpendicular polarizers (not shown) may be provided between the illumination source 122 and the imaging path to emphasize diffuse skin reflection, as well as sub-surface scattering. Since the red and green wavelengths penetrate deeper into the skin, apertures 118a and 118b may be dedicated to transmitting red light may be disposed with a polarizer that is perpendicular with respect to a polarizer disposed with the red LED 122. Similarly, apertures 114a and 114b may be dedicated to transmitting green light and may be disposed with a polarizer that is perpendicular with respect to a polarizer disposed with the green LED 122.

For example, polarization may be used to capture images for measuring hemoglobin and melanin concentrations of the skin 110. Thus, skin surface 110 may be illuminated using the red and green LEDs 122, and the resulting diffused and/or scattered reflection from deeper layers of skin surface 110 may be transmitted via apertures 118b and 114b, respectively, and imaged at sensor 108b, or at regions of sensor 108. These images may be analyzed by processor 112 to measure the hemoglobin and melanin levels, and superimposed by processor 112 as 'layers' on the 3D model reconstructed above.

The color characterization of skin surface 110 may be measured using multi-spectral acquisition, by sequentially or simultaneously illuminating the skin surface 110 using each of the red, blue, and green LEDs 122. Each reflected wavelength may be separately transmitted via one aperture of its respective dedicated aperture pair, 114, 116, and 118, and detected by mono sensor 108. Optionally, three images: one image per wavelength, may be superimposed to create a two-dimensional (2D) color image of skin sample 110 which may be combined with the 3D model and optionally with the hemoglobin and/or melanin reconstruction, to create a multi-layer 3D reconstruction of skin sample 110. For example, images captured at sensor 108a via apertures 114a, 116a, and 118a may be used for the 2D color image, and which may be overlaid on the 3D reconstruction as a color layer. Images captured at sensor 108b via apertures 114b, 116b, and 118b may be used for subsurface analyzing of the skin.

Optionally, white light may be synthesized from suitable ratios of illumination by the red, green, and blue LEDs. When acquiring the multi-layer images, LEDs 122 may be synchronized with one or more shutters of camera 100 or 200. The shutters may operate in short pulses corresponding to the red green and blue illumination sequence. Optionally, for each pulse, both sides 108a and 108b of sensor 108 may simultaneously capture two stereo images corresponding to the two optical paths via any of the aperture pairs of mask 104.

Imaging thus in stereo using varying wavelengths and/or polarization may allow detecting both depth and spectral characterization of object 110.

Figure 9E:
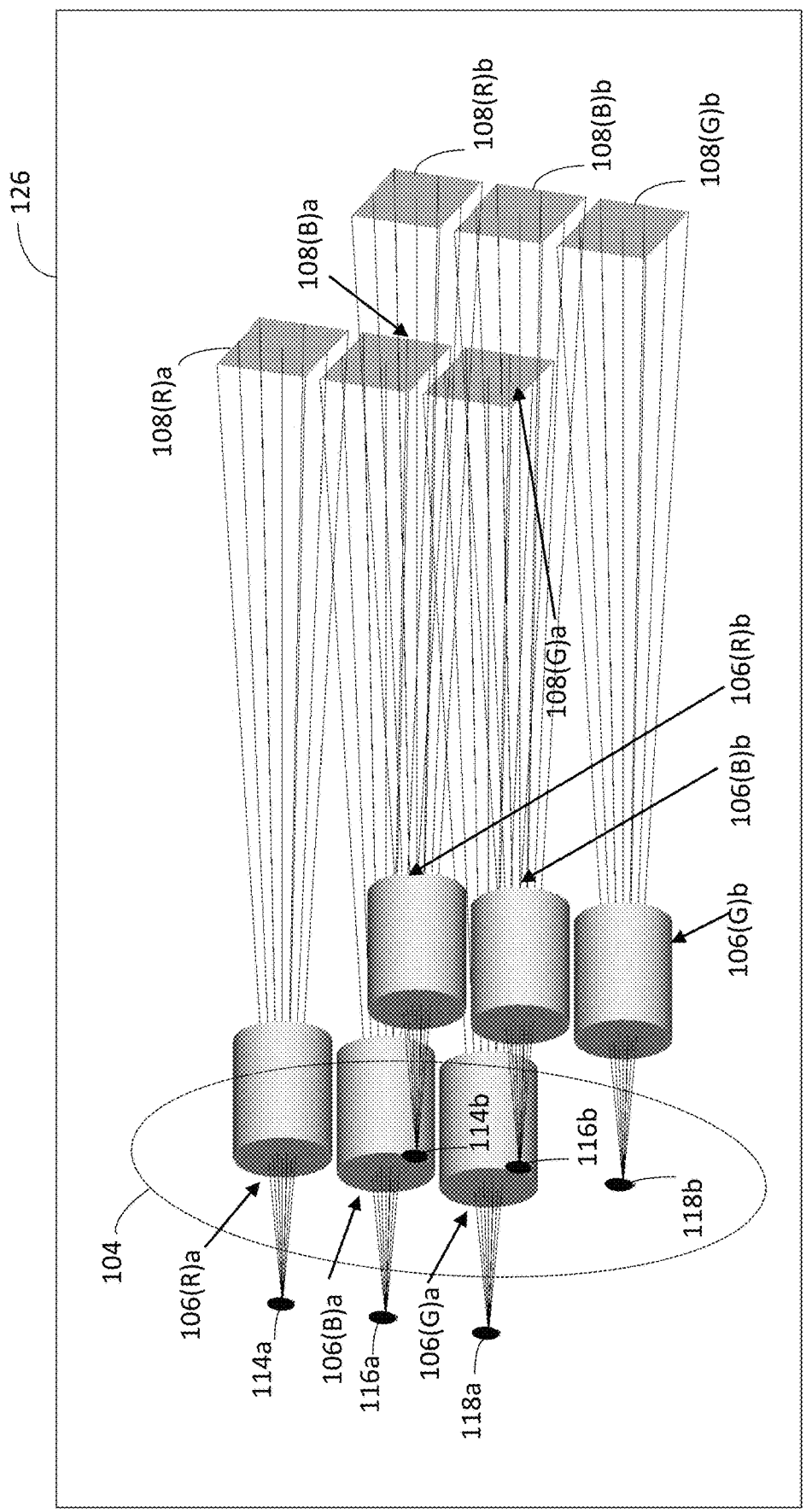
FIGS. 9E-9F show a configuration of an optical apparatus configured with the system of FIG. 9A, in accordance with an embodiment.
Figure 9F:
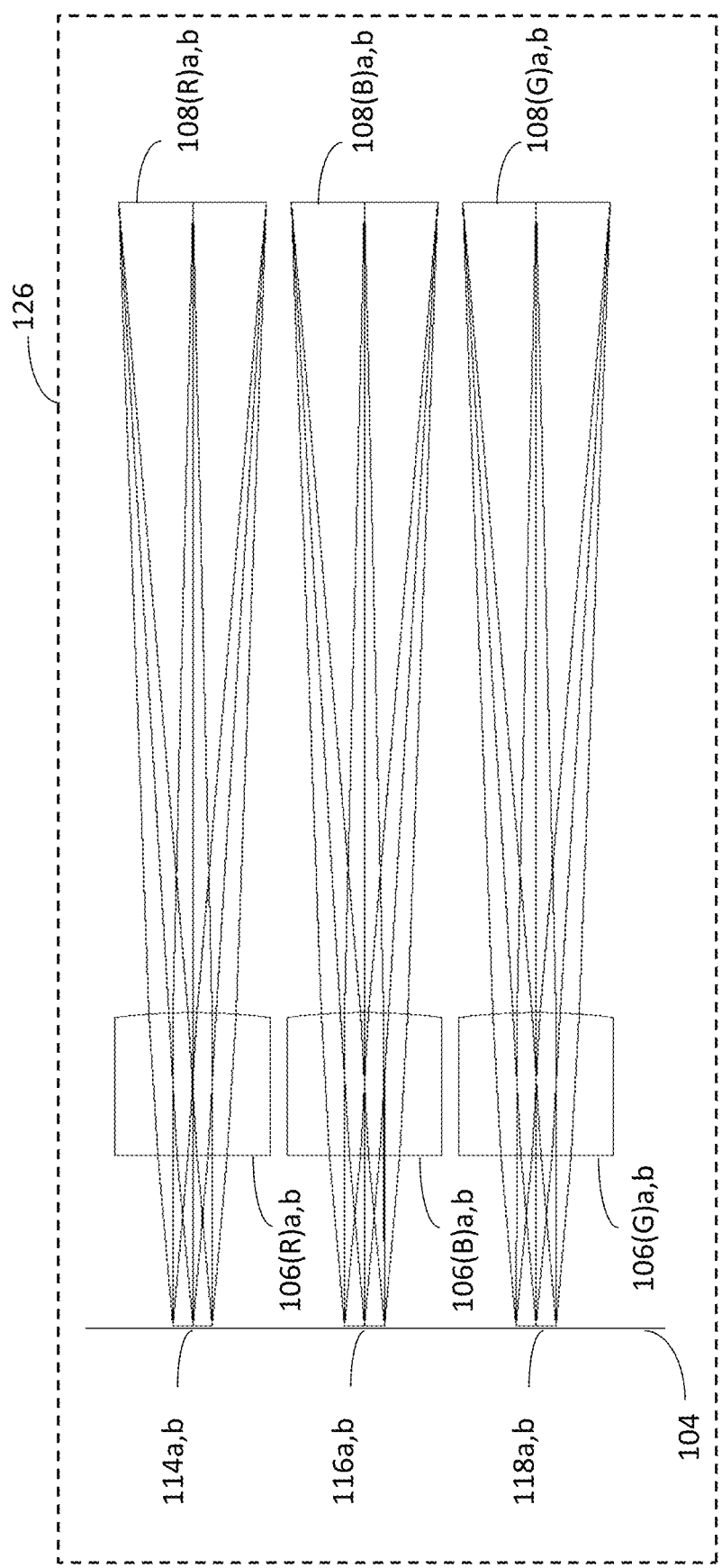

Referring to FIGS. 9E and 9F, another configuration for optical apparatus 126 is shown (in perspective and side views, respectively), having 6 sensors, 108a-108f, each dedicated to a different one of the six apertures 114a, 114b, 116a, 116b, 118a, 118b of mask 104. The apertures are shown having a uniform size and shape for illustrative purposes only, and may optionally have differing sizes and shapes as described above. Optionally, each aperture pair may be provided with a different color filter and/or polarizer corresponding to LEDs 122, as described above. Each aperture 114a, 114b, 116a, 116b, 118a, 118b may have a dedicated back lens, 106(R)a, 106(B)a, 106(G)a, 106(R)b, 106(B)b, and 106(G)b, respectively, shown as two sets of three back lenses corresponding to stereo three-color detection, where 'R' is understood to represent red, 'B' is understood to represent blue, and 'G' is understood to represent green. Each lens may be aligned to separately focus light from each of the six apertures and produce an image on different dedicated sensors 108a-108f, or different regions of sensor 108.

Thus, in one embodiment, apertures 114a and 114b may optionally be provided with a red color filter and optionally a polarizing component (not shown) corresponding to a polarizing component disposed with red LED 122. Sensors 108(R)a and 108(R)b may be aligned to sense red light emitted via apertures 114a and 114b and focused via lenses 106(R)a and 106(R)b and capture red stereo images of surface 110. Apertures 116a and 116b may be provided with a blue color filter and optionally a polarizing component (not shown) corresponding to a polarizing component disposed with blue LED 122. Sensors 108(B)a and 108(B)b may be aligned to sense light emitted via apertures 116a and 116b, and focused via lenses 106(B)a and 106(B)b and dedicated to capturing blue stereo images of surface 110. Apertures 118a and 118b may be provided with a green color filter and optionally a polarizing component (not shown) corresponding to a polarizing component disposed with green LED 122. Sensors 108(G)a and 108(G)b may be aligned to sense light emitted via apertures 118a and 118b and focused via lenses 106(G)a and 106(G)b, and dedicated to capturing green stereo images of surface 110. The multiple images captured thus, optionally simultaneously, may be used to construct a multi-layer, high resolution, 3D image of surface 110. It may be appreciated that the order of the colors is arbitrary and other arrangements may be used.

Figure 9G:
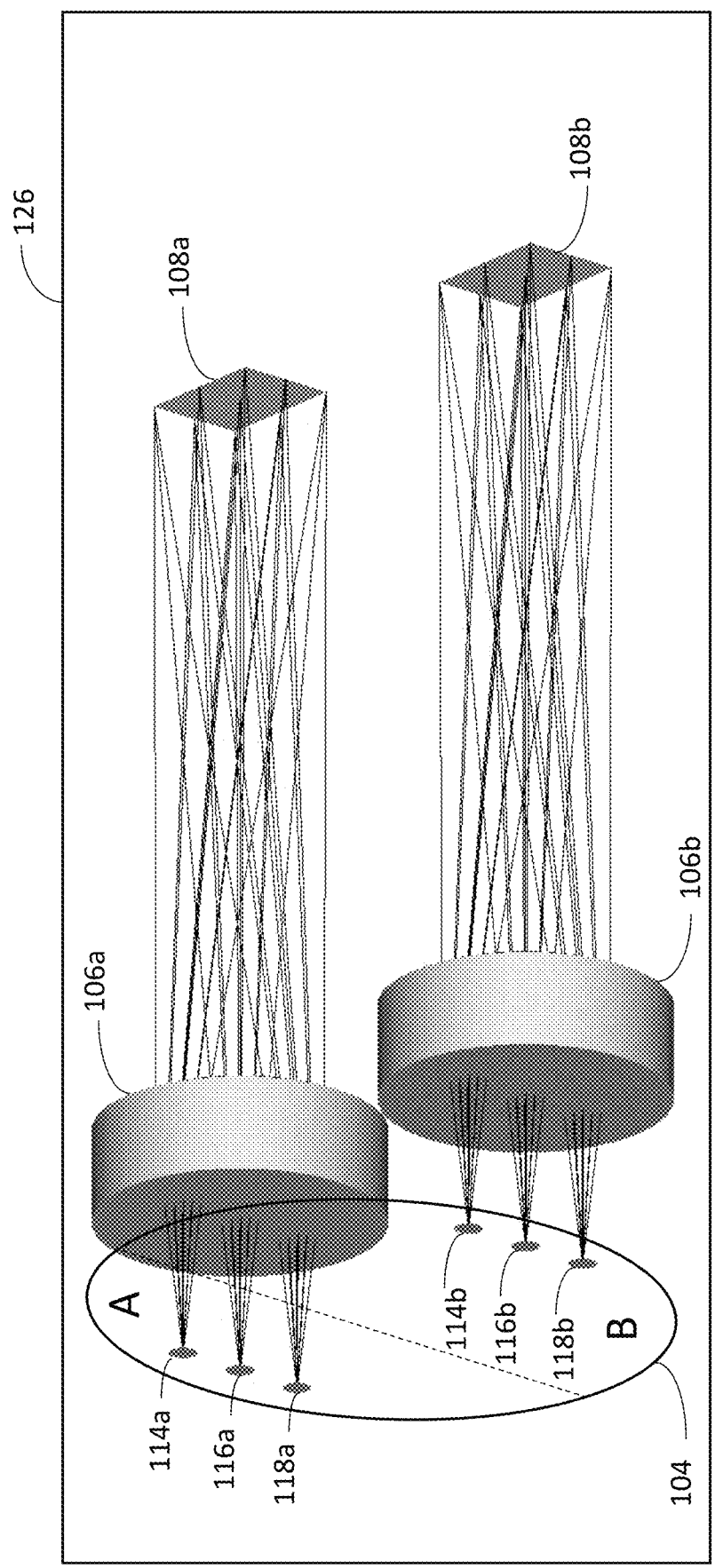
FIG. 9G shows another configuration of an optical apparatus configured with the system of FIG. 9A, in accordance with an embodiment.

Reference is now made to FIG. 9G, which shows another configuration for optical apparatus 126. The system of FIG. 9G is substantially similar to that of FIGS. 9E-9F with the noted exception that two lenses and two sensors are provided, a shared lens and sensor dedicated to each of the two imaging systems or stereoscopic views, corresponding to each side A, B, of mask 104. Light passing through the apertures 114a, 116a, and 118a on side A of the mask 104 and the dedicated lens 106a will reach sensor 108a at the same position but different angles. Similarly, light passing through the apertures 114b, 116b, and 118b on side B of mask 104 and the dedicated lens 106b will reach sensor 108b at the same position but different angles. Detecting the light from multiple different directions may enhance the reconstruction of the 3D map of object 110.

In this configuration, LEDs 122 may illuminate the surface sequentially, allowing sensors 108a and 108b to simultaneously capture a pair of images for each illuminating LED 122, precluding the need to provide color filters with mask 104.

Reference is now made to FIGS. 10A-10D, each showing three RGB cycles for multi-layer image acquisition using the mask of FIG. 9C. FIG. 10A generally illustrates the cycles; FIG. 10B illustrates the cycles without polarization; FIG. 10C illustrates the cycles at sensor 108a with certain polarization; and FIG. 10D illustrates the cycles at sensor 108b with certain polarization.

Image acquisition by sensors 108a and 108b may be synchronized with illumination source 112. For example, processor 112 may synchronize illumination source 122 with a shutter (not shown) of camera 300. FIG. 10A shows three illumination cycles of surface 110, each cycle comprising sequential blue, red, and green illumination pulses by the colored LEDs of illumination source 122 for a total of 9 pulses. FIGS. 10C and 10D each show three image acquisition cycles by sensors 108a and 108b, respectively, synchronized with the illumination cycles of FIG. 10A, resulting in the acquisition of an image per pulse for each sensor. Apertures of mask 104 corresponding to images acquired using parallel-polarized light are indicated as 'P', and apertures of mask 104 images acquired using cross-polarized light are indicated as 'S'. The parallel-polarized illumination allows measuring the skin surface color and/or depth corresponding to the specular reflection, and the polarized illumination allows measuring light that has penetrated into deeper parts of the skin.

As seen in FIGS. 10A-10D, for each illuminating pulse by any of the LEDs of illumination source 122, two images are simultaneously captured via the two optical paths described above: one image captured at sensor 108A and the other image captured at sensor 108B. Each pair of acquired images may be used to measure different characteristics of object 110, and which may be processed by processor 112 to reconstruct a multi-layered 3D model of object 110. Thus, in FIGS. 10C-10D, for each blue illumination pulse, two parallel-polarized images are captured, one image at each of sensors 108a and 108b. The disparity between these images may be used to calculate the depth characteristic of object 110. For each of the red and green illumination pulses, the image captured at sensor 108a is acquired using parallel-polarized light, and the image captured at sensor 108b is acquired using cross-polarized light compared to the polarizer on the LED's. These images may be used to measure features or characteristics beneath the skin's surface.

Processor 112 may receive and register the images acquired above into an RGB image. The first step after calculating the disparity and the depth map obtained by applying Eq. 1 to the images captured by apertures 116a and 116b, may be to shift images captured by different apertures using the depth map results by the following equation:

$$\text{shift}(i, j) = \frac{(z(i, j) - F_1)F_2 b}{F_1^2} \quad (6)$$

Where (i, j) are the index of the pixel on the image, z is the depth calculated from the disparity map and $F_1$ and $F_2$ are the focal lengths as described by Eq. 1.

Optionally, the relative position of each of the acquired images may be obtained, such as by detecting their respective offset and rotation. This may be implemented by searching the relative position for each image that maximizes the correlation between each image pair simultaneously acquired for each illumination pulse.

Figure 11A:
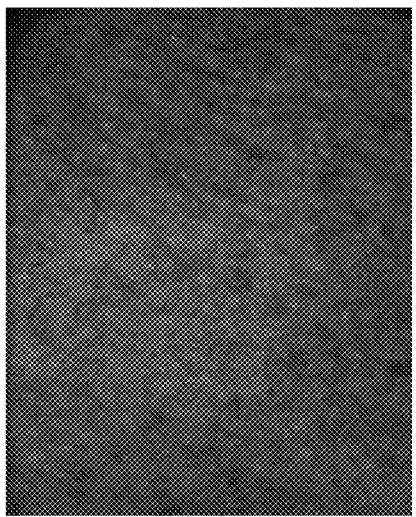
FIGS. 11A-11C show images of the same skin surface captured under blue, green, and red illumination, respectively.
Figure 11B:
Figure 11C:
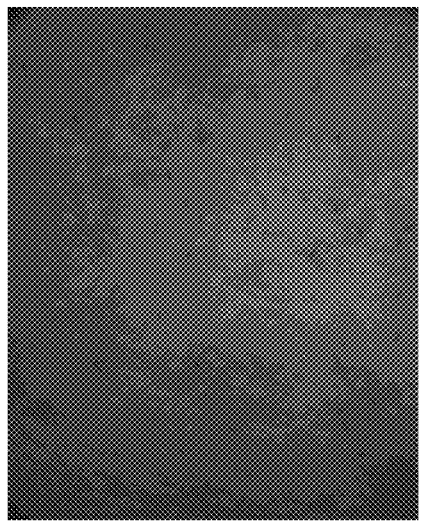

Optionally, if the discrepancies between the images is large, a direct correlation may be difficult to calculate. Referring to FIGS. 11A-11C, images of the same skin surface captured by sensor 108 under blue, green, and red illumination, respectively, are shown. It may be appreciated that the discrepancies between the three images may pose a challenge to calculating a direct correlation therebetween. To overcome this, processor 112 may apply one or more image processing techniques, such as but not limited to, edge enhancement and equalization. For example, processor 112 may perform the following steps:

1. Calculate variance map for each color,
2. Scale all variance maps into the same dynamic range, and
3. Find relative positions that maximize correlation.

Figure 12:
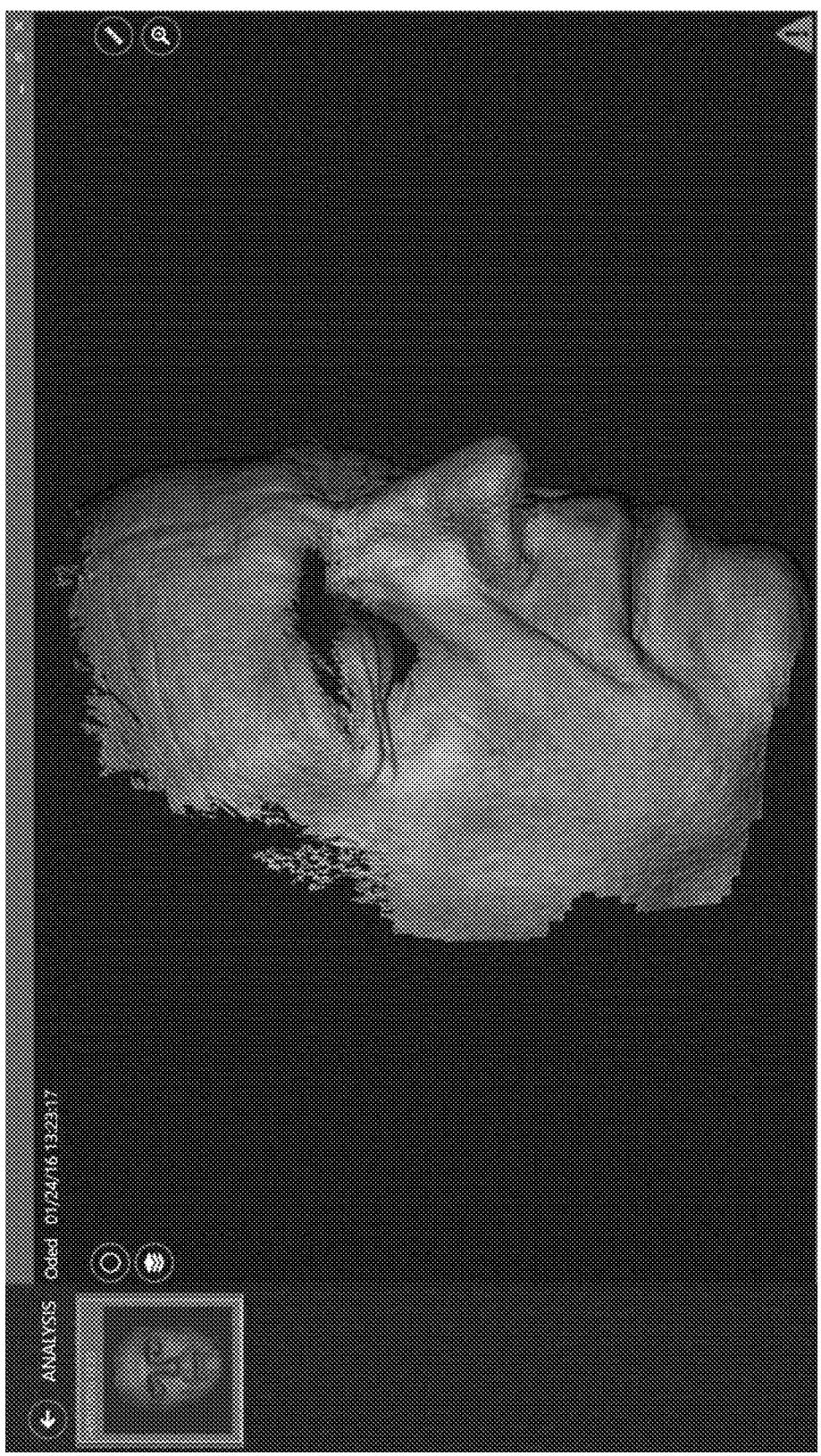
FIG. 12 shows an exemplary multi-layer 3D reconstruction using the system and method described herein.

The resulting processed images may be used to reconstruct the 3D model. Referring to FIG. 12, an exemplary multi-layer 3D reconstruction is shown, using the system and method described above.

Figure 13A:
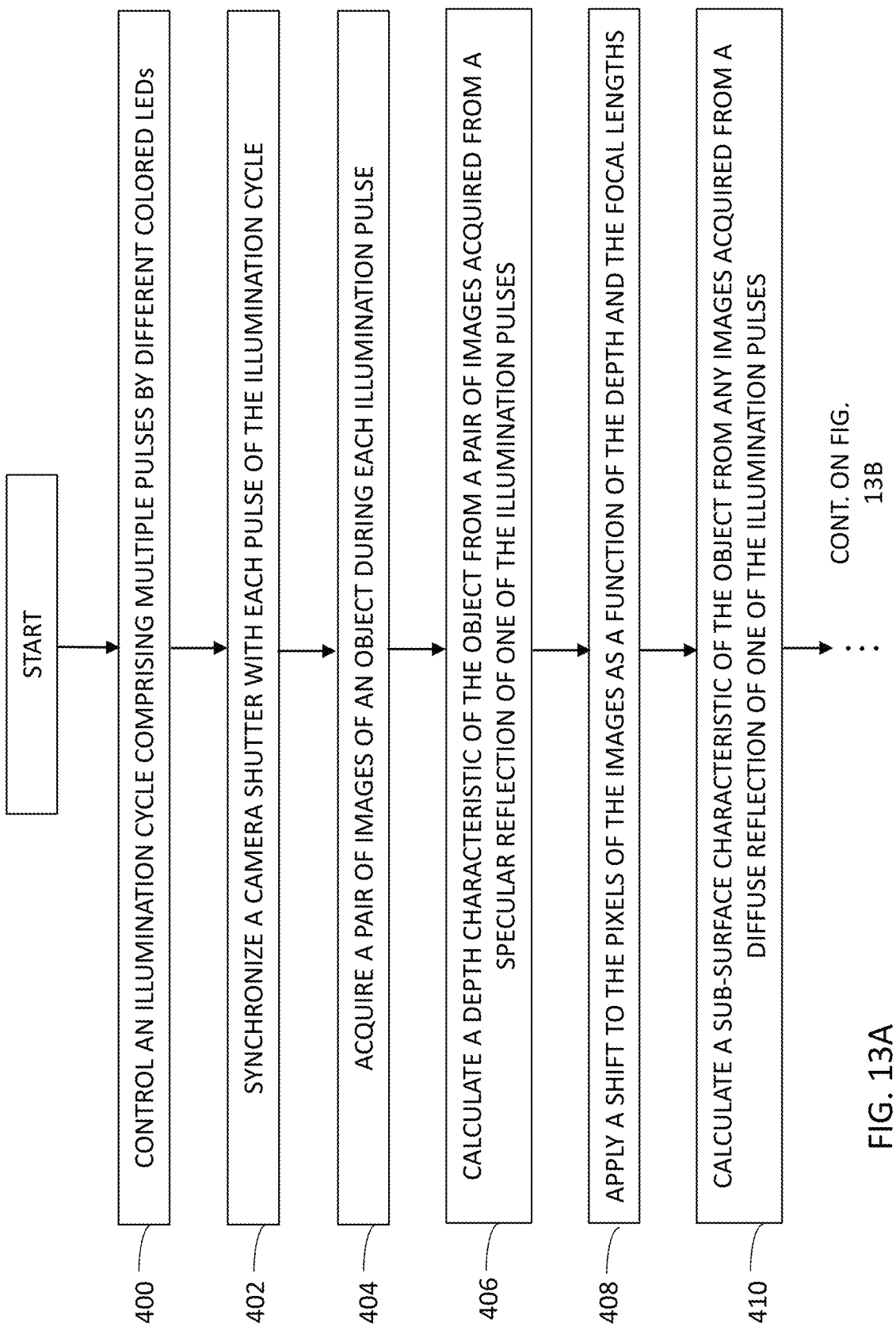
FIGS. 13A-B taken together, show a flowchart of a method for creating a multi-layer 3D reconstruction of an object, in accordance with an embodiment.
Figure 13B:
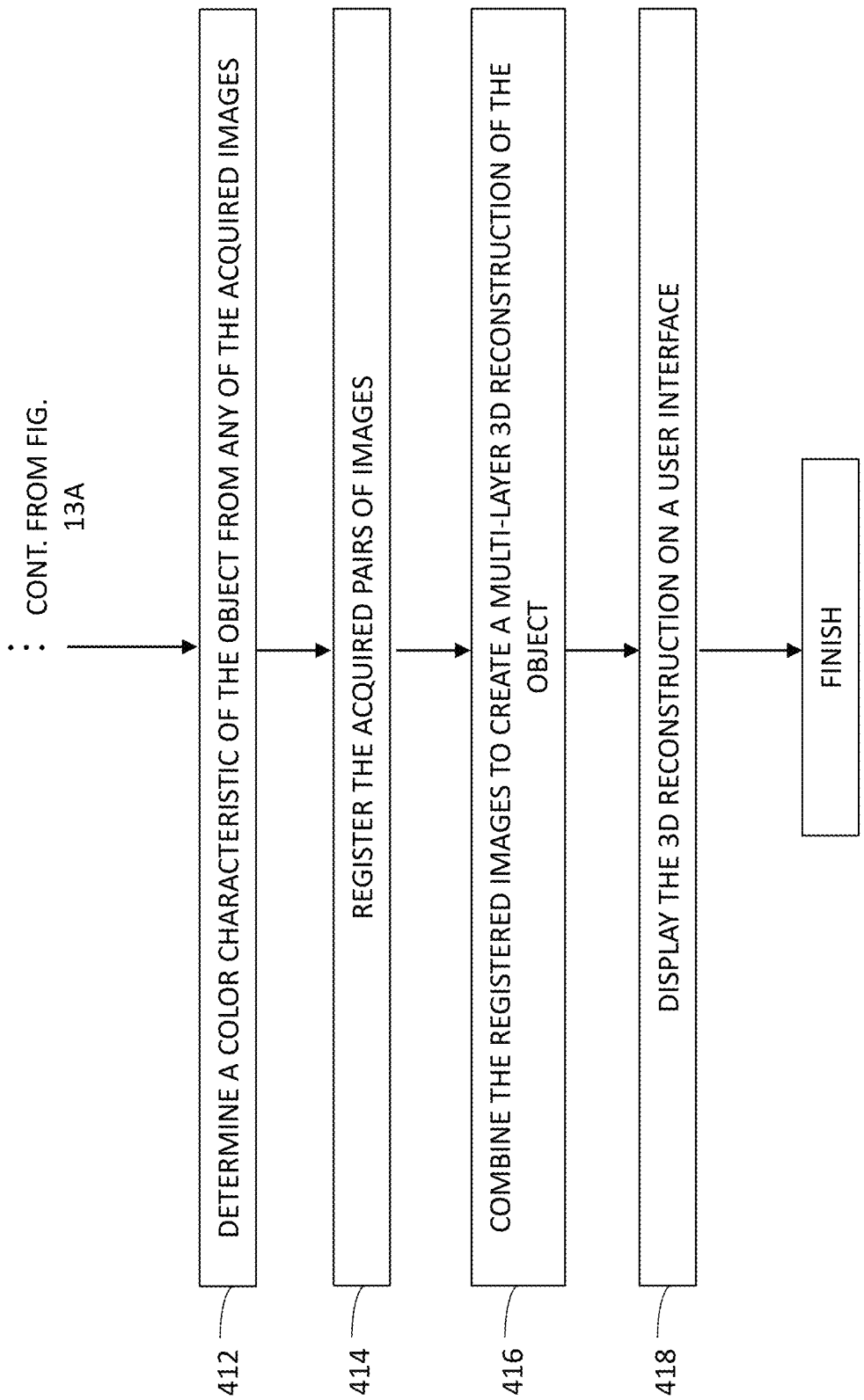

Reference is now made to FIGS. 13A-B which taken together, show a flowchart of a method for creating a multi-layer 3D reconstruction of an object, in accordance with an embodiment, and which may be implemented by one or more processors, such as processor 112. An illumination cycle comprising controlling the illumination of multiple different colored LEDs may be controlled. For example, the illumination cycle may comprise any combination of a blue illumination pulse by a blue LED, a green illumination pulse by a green LED, and a red illumination pulse by a red LED (Step 400). A camera shutter may be synchronized with each illumination pulse of the illumination cycle (Step 402). A pair of images of an object may be acquired during each illumination pulse (Step 404). For example, the images may be acquired via a single mono sensor divided into two portions and configured with a stereo imaging system. Optionally, one or more images acquired during the illumination cycle may be acquired from polarized light. Optionally, the polarized light corresponds to the blue illumination pulse, or any of the green and red illumination pulses.

A depth characteristic of the object may be calculated from one of the pairs of images acquired from a specular reflection of one of the illumination pulses (Step 406). The pixels of the captured images may be shifted as a function of the depth characteristic, and the focal lengths $F_1$ and $F_2$ of Eq. 1. (Step 408). For example, the specular reflection may correspond to the blue illumination pulse. A sub-surface quality of the object may be measured using any images acquired from a diffuse reflection of one of the illumination pulses (Step 410). For example, the diffuse reflection may correspond to any of the green and red illumination pulses and the subsurface quality may comprise any of melanin and hemoglobin. A color characteristic of the object may be determined from any of the acquired images (Step 412). For example, the color characteristic may be determined from the image pair acquired during the blue illumination pulse, or from one or more images acquired during a single illumination cycle. For example, the color characteristic may be determined from one image from each pair of images acquired during each of the blue, red, and green illumination pulses.

The pairs of images acquired over multiple illumination cycles may be registered (Step 414). Optionally, any of an edge enhancement technique, an equalization technique, and an image correlation technique comprising: a) calculating a variance map for each color, b) scaling the variance maps to the same dynamic range, and c) finding the relative positions of detected features to maximize correlation may be applied to the registered image pairs. The registered pairs of images may be combined to create a multi-layer 3D reconstruction of the object (Step 416). The 3D reconstruction may be displayed on a user interface (Step 418).

The present invention may be a system, a method, and/or a computer program product. The computer program product may include a computer readable storage medium (or media) having computer readable program instructions thereon for causing a processor to carry out aspects of the present invention.

The computer readable storage medium can be a non-transitory, tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, or any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention may be described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system, comprising:
   A. a camera configured to operate under telecentric conditions, said camera comprises:
      two imaging systems each comprising a different optical path corresponding to a different viewing angle of an object;
      multiple illumination sources;
      a mask comprising multiple pairs of apertures, wherein each aperture of each aperture pair corresponds to a different one of the imaging systems, wherein each aperture of each of said pairs of apertures is configured to transmit a light pulse from a different optical path to at least one imaging sensor, wherein said multiple pairs of apertures are positioned symmetrically opposite about the viewing axis of said camera; and
      at least one detector configured to acquire multiple image pairs of the object from the two imaging systems via the multiple pairs of apertures; and
   B. a processor configured to produce, from the multiple acquired image pairs, a multi-layer three dimensional reconstruction of the object
   wherein said viewing angle is between 3 and 9 degrees.

2. The system of claim 1, wherein each pair of apertures is dedicated to a different one of the multiple illumination sources.

3. The system according to claim 1, where said multiple illumination sources comprise a red LED, a green LED, and a blue LED.

4. The system of claim 3, wherein each of the multiple different LEDs has a full-width-at-half (FWHM) bandwidth of 10 nm±10%.

5. The system according to claim 1, wherein the at least one detector comprises a mono sensor having a dedicated region for each aperture, and configured to simultaneously capture multiple images comprising an image for each of the multiple illumination sources and for each of the imaging systems.

6. The system according to claim 1, wherein the at least one detector comprises two imaging sensors that are each dedicated to one of the imaging systems and are configured to simultaneously detect an image pair for each of the illumination sources.

7. The system according to claim 1, wherein the at least one detector comprises an imaging sensor having multiple sensor regions, each sensor region dedicated to a different one of the multiple apertures, and wherein the multiple sensor regions are configured to simultaneously capture multiple images comprising an image for each of the multiple illumination sources and for each of the imaging systems.

8. The system according to claim 1, wherein at least one of the multiple different illumination sources is disposed with a polarization component, and wherein at least one of the apertures dedicated to the illumination source disposed with the polarization component, is disposed with a complementary polarization component.

9. The system of claim 8, wherein the at least one of the apertures disposed with the polarization component is dedicated to a blue light source.

10. The system according to claim 1, wherein each pair of apertures is disposed with a color filter corresponding to its dedicated illumination source.

11. The system according to claim 1, further comprising at least one back lens configured to focus light transmitted via the multiple pairs of apertures of the mask to the at least one detector.

12. The system according to claim 1, wherein at least one image pair of the acquired image pairs corresponds to a specular reflection off the object, and wherein the processor is further configured to use the at least one image pair to measure a depth characteristic of the object.

13. The system of claim 12, wherein the processor is further configured to apply a shift to the pixels of the acquired image as a function of the depth characteristic.

14. The system according to claim 1, wherein at least one of the acquired images corresponds to a diffuse reflection off the object, and wherein the processor is further configured to use the at least one acquired image to measure a hemoglobin level of the object.

15. The system according to claim 1, wherein at least one of the acquired images corresponds to a diffuse reflection off the object, and wherein the processor is further configured to use the at least acquired one image to measure a melanin level of the object.

16. The system according to claim 1, wherein the processor is configured to use at least one of the acquired images to measure a color characteristic of the object.

17. The system according to claim 1, wherein the processor is configured to synchronize the illumination source with a shutter of the camera.

18. The system according to claim 1, further comprising a user interface configured to display the multi-layer three dimensional reconstruction of the object.

19. The system according to claim 1, wherein said processor is configured to produce a three-dimensional (3D) point cloud representing the object, based, at least in part, on said multiple image pairs of the object.

20. The system according to claim 19, wherein said multiple image pairs of the object are a series of consecutive image pairs each representing a region of said object, wherein said processor is configured to produce a 3D point from each image pair of the series of consecutive image pairs, and wherein said processor is further configured to add all the 3D point clouds together into a single 3D point cloud representing said object.

* * * * *